US012778522B2

(12) United States Patent
Konkle et al.

(10) Patent No.: US 12,778,522 B2
(45) Date of Patent: Nov. 3, 2026

(54) METHODS AND SYSTEMS FOR REDUCED INTERNAL SCATTER CROSSTALK

(71) Applicant: GE Precision Healthcare LLC, Waukesha, WI (US)

(72) Inventors: Nicholas Konkle, Sussex, WI (US); Jonathan Maltz, Oakland, CA (US); Bruno De Man, Niskayuna, NY (US); Sathish Ramani, Niskayuna, NY (US); Mingye Wu, Clifton Park, NY (US); Brian Yanoff, Niskayuna, NY (US); Marc Schaepkens, West Milwaukee, WI (US); William Hennessy, Troy, NY (US); Biju Jacob, Niskayuna, NY (US)

(73) Assignee: GE PRECISION HEALTHCARE LLC, Waukesha, WI (US)

( * ) Notice: Subject to any disclaimer, the term of this patent is extended or adjusted under 35 U.S.C. 154(b) by 180 days.

(21) Appl. No.: 18/627,323

(22) Filed: Apr. 4, 2024

(65) Prior Publication Data

US 2025/0311986 A1 Oct. 9, 2025

(51) Int. Cl.

| | |
|---|---|
| ***A61B 6/03*** | (2006.01) |
| ***A61B 6/00*** | (2024.01) |
| ***A61B 6/42*** | (2024.01) |
| ***G01T 1/24*** | (2006.01) |

(52) U.S. Cl.

CPC ............ *A61B 6/032* (2013.01); *A61B 6/4241* (2013.01); *A61B 6/4266* (2013.01); *A61B 6/4291* (2013.01); *A61B 6/4447* (2013.01); *G01T 1/244* (2013.01)

(58) Field of Classification Search

CPC ..... A61B 6/032; A61B 6/4241; A61B 6/4266; A61B 6/4291; A61B 6/4447; A61B 6/4014

See application file for complete search history.

(56) References Cited

U.S. PATENT DOCUMENTS

| | | | | |
|---|---|---|---|---|
| 8,564,084 | B2 | 10/2013 | Vogtmeier et al. | |
| 9,089,266 | B2 * | 7/2015 | Zou | A61B 6/032 |
| 10,422,887 | B2 | 9/2019 | Persson et al. | |
| 10,433,811 | B2 | 10/2019 | Jacob et al. | |
| 10,631,815 | B2 | 4/2020 | Rui et al. | |
| 11,389,125 | B1 * | 7/2022 | Yanoff | G01T 1/244 |
| 2018/0136340 | A1 * | 5/2018 | Nelson | G01T 1/1611 |
| 2020/0093448 | A1 | 3/2020 | Suyama | |
| 2021/0244373 | A1 * | 8/2021 | Wiedmann | G01T 1/241 |
| 2023/0162880 | A1 | 5/2023 | Maria | |
| 2023/0363728 | A1 * | 11/2023 | Jacob | G21K 1/04 |
| 2024/0148342 | A1 * | 5/2024 | Li | A61B 6/483 |
| 2025/0052916 | A1 * | 2/2025 | Yanoff | G01T 1/242 |

OTHER PUBLICATIONS

EP application 25163767.4 filed Mar. 14, 2025—partial Search Report issued Aug. 1, 2025, 15 pages.

* cited by examiner

*Primary Examiner* — Casey Bryant

(74) *Attorney, Agent, or Firm* — McCoy Russell LLP

(57) ABSTRACT

Systems are provided for a computed tomography system, comprising a gantry configured to rotate around an axis of rotation and a detector array comprised of a plurality of photon-counting computed tomography (PCCT) detector units configured to be rotated around the axis of rotation by the gantry, wherein a stacking axis of least one of the plurality of PCCT detector arrays is positioned at an angle with respect to the axis of rotation.

11 Claims, 18 Drawing Sheets

METHODS AND SYSTEMS FOR REDUCED INTERNAL SCATTER CROSSTALK

TECHNICAL FIELD

Embodiments of the subject matter disclosed herein relate to systems and methods for reducing scatter crosstalk internal to a photon counting computed tomography sensor.

BACKGROUND

A photon counting computed tomography (PCCT) detecting unit may include a plurality of sensors and each sensor may be subdivided into sensor subunits (e.g., pixels). A patient may be positioned between an X-ray source and the PCCT detecting unit. X-rays may scatter off the patient and are detected by the PCCT detecting unit. The active material of the sensor is a semiconductor (e.g., silicon) which directly converts energy of the incoming X-ray photons into electrical signals. A source of noise of PCCT images may be signals from X-ray photons that are further scattered off of the sensor and then converted to electrical signals. An anti-scattering grid may be positioned between sensors of the PCCT detecting unit to absorb the X-ray photons scattered between sensors. However, the anti-scatter grid does not prevent internal scatter between sensor subunits within a sensor of the PCCT detecting unit. The internal scatter may cause stochastic noise which is challenging to correct for and erodes detail of a collected image.

BRIEF DESCRIPTION

In one embodiment, a computed tomography system may comprise a gantry configured to rotate around an axis of rotation and a detector array comprised of a plurality of photon-counting computed tomography (PCCT) detector units configured to be rotated around the axis of rotation by the gantry, wherein a stacking axis of least one of the plurality of PCCT detector arrays is positioned at an angle with respect to the axis of rotation. In this way, effects of internal scatter may be reduced, resulting in a higher resolution, or more detailed, image.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, herein below.

DETAILED DESCRIPTION

Figure 1:
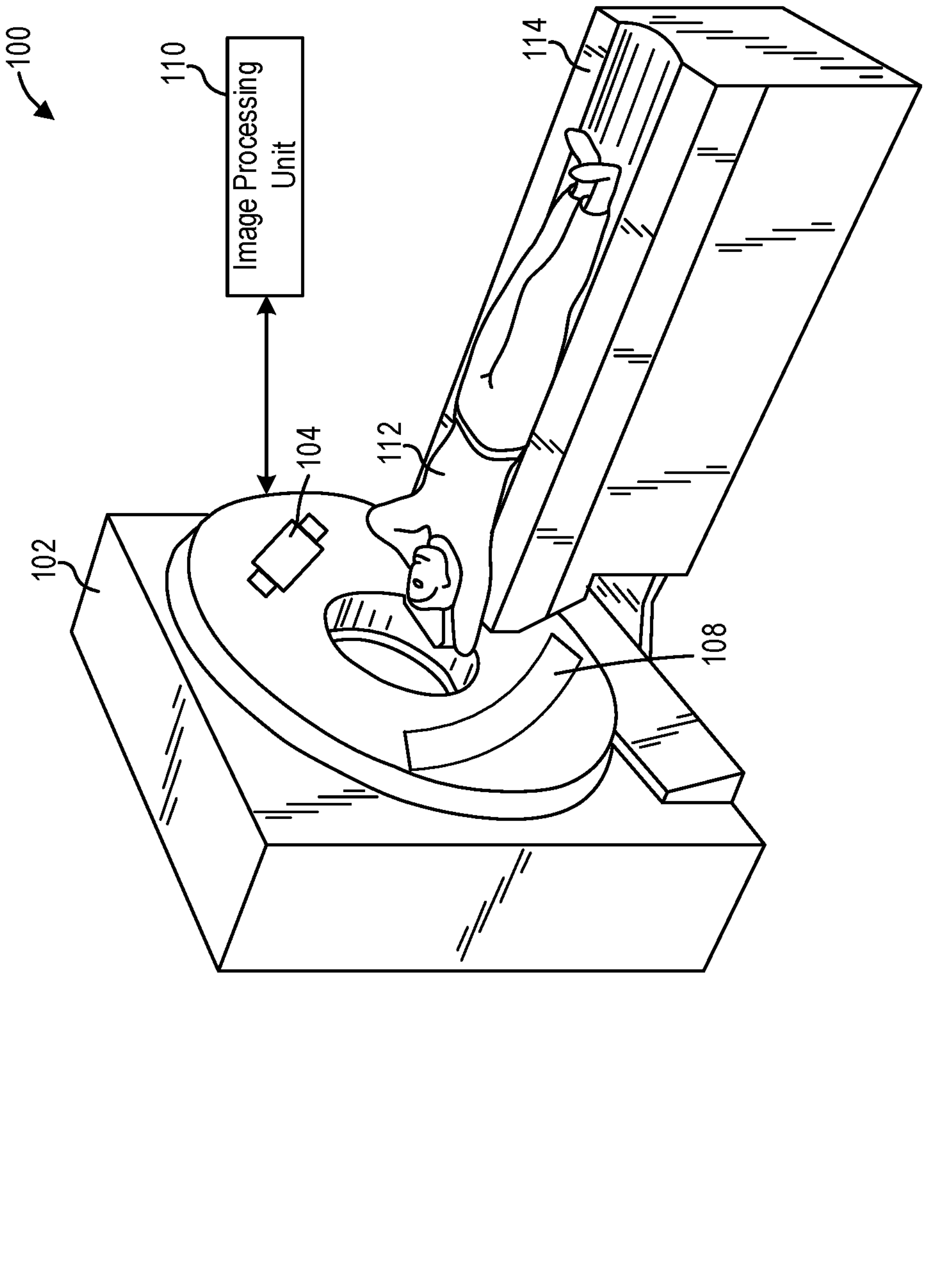
FIG. 1 shows a pictorial view of a CT imaging system, in accordance with one or more embodiments of the present disclosure.
Figure 2:
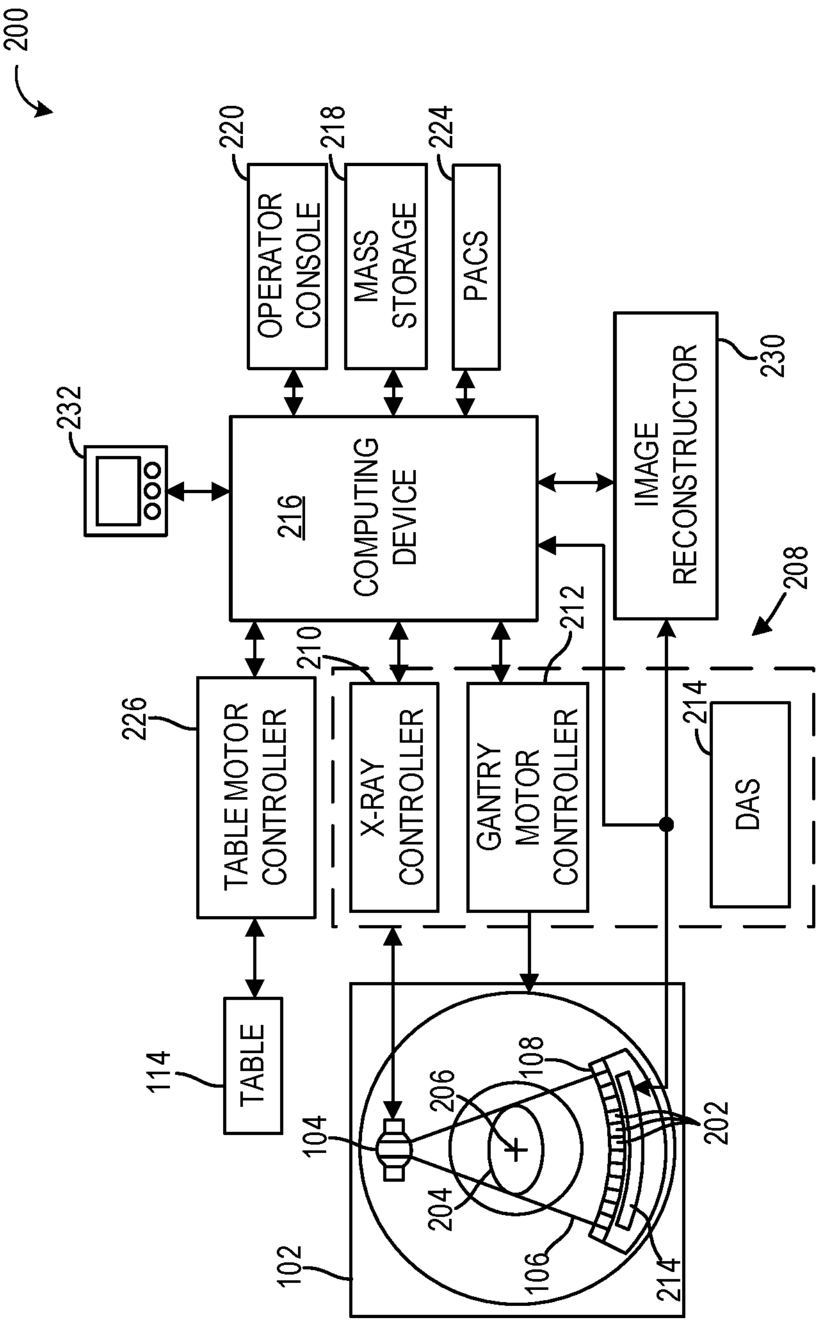
FIG. 2 shows a block schematic diagram of an exemplary CT imaging system, in accordance with one or more embodiments of the present disclosure.
Figure 3:
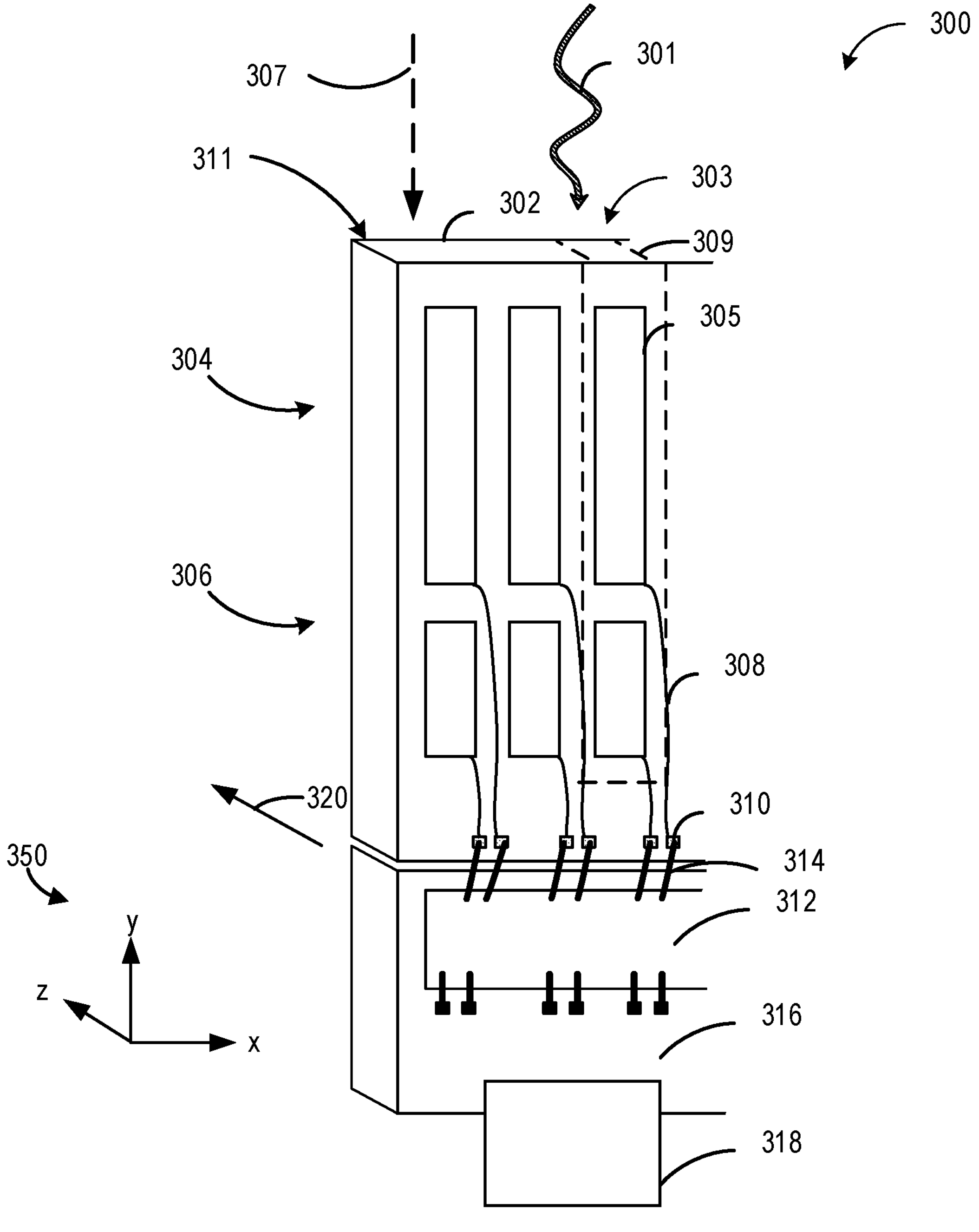
FIG. 3 shows a diagram of a sensor of a photon-counting computed tomography (PCCT) detector unit.
Figure 4:
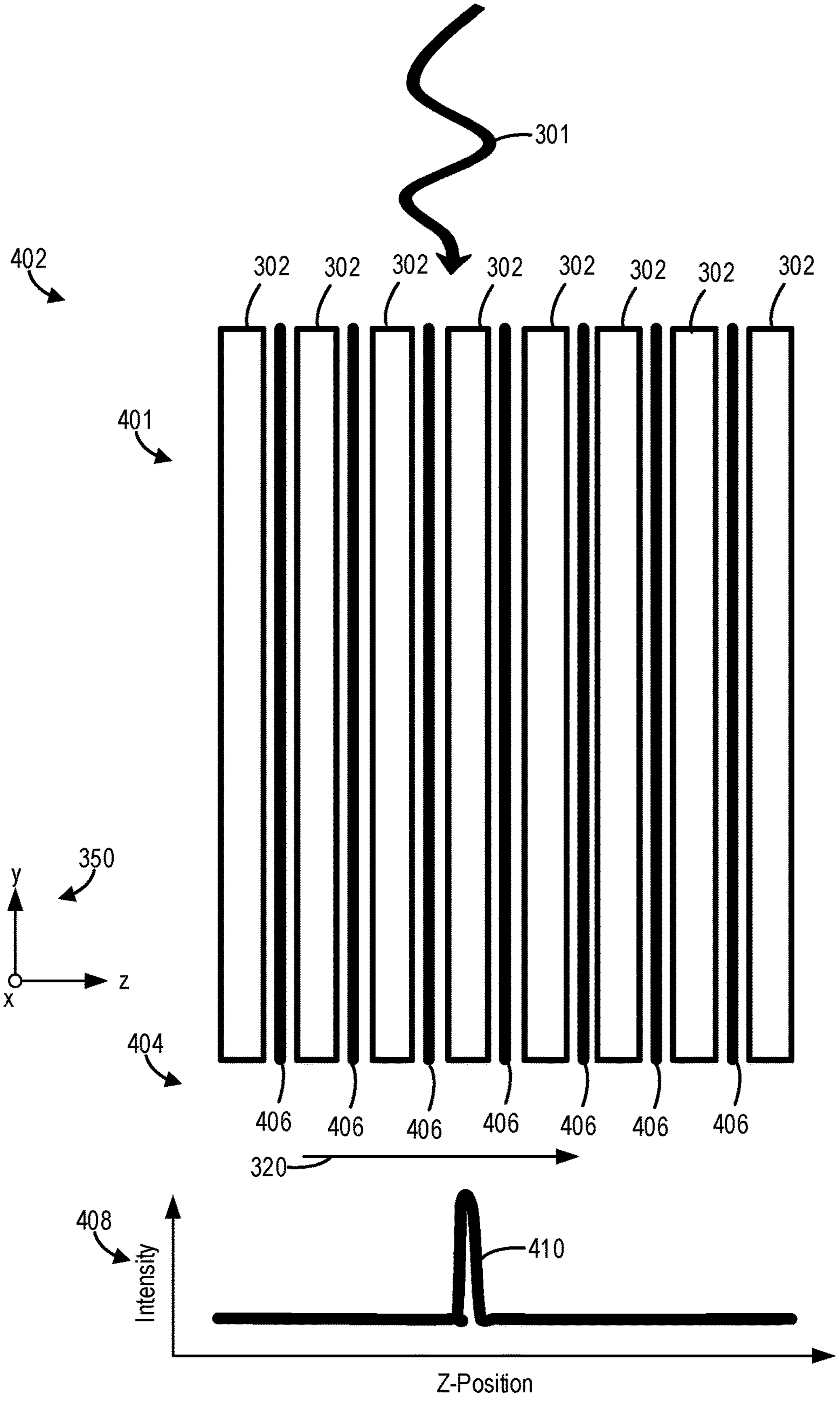
FIG. 4 shows a first perspective view of sensors of a PCCT detector unit and related scattering.
Figure 5:
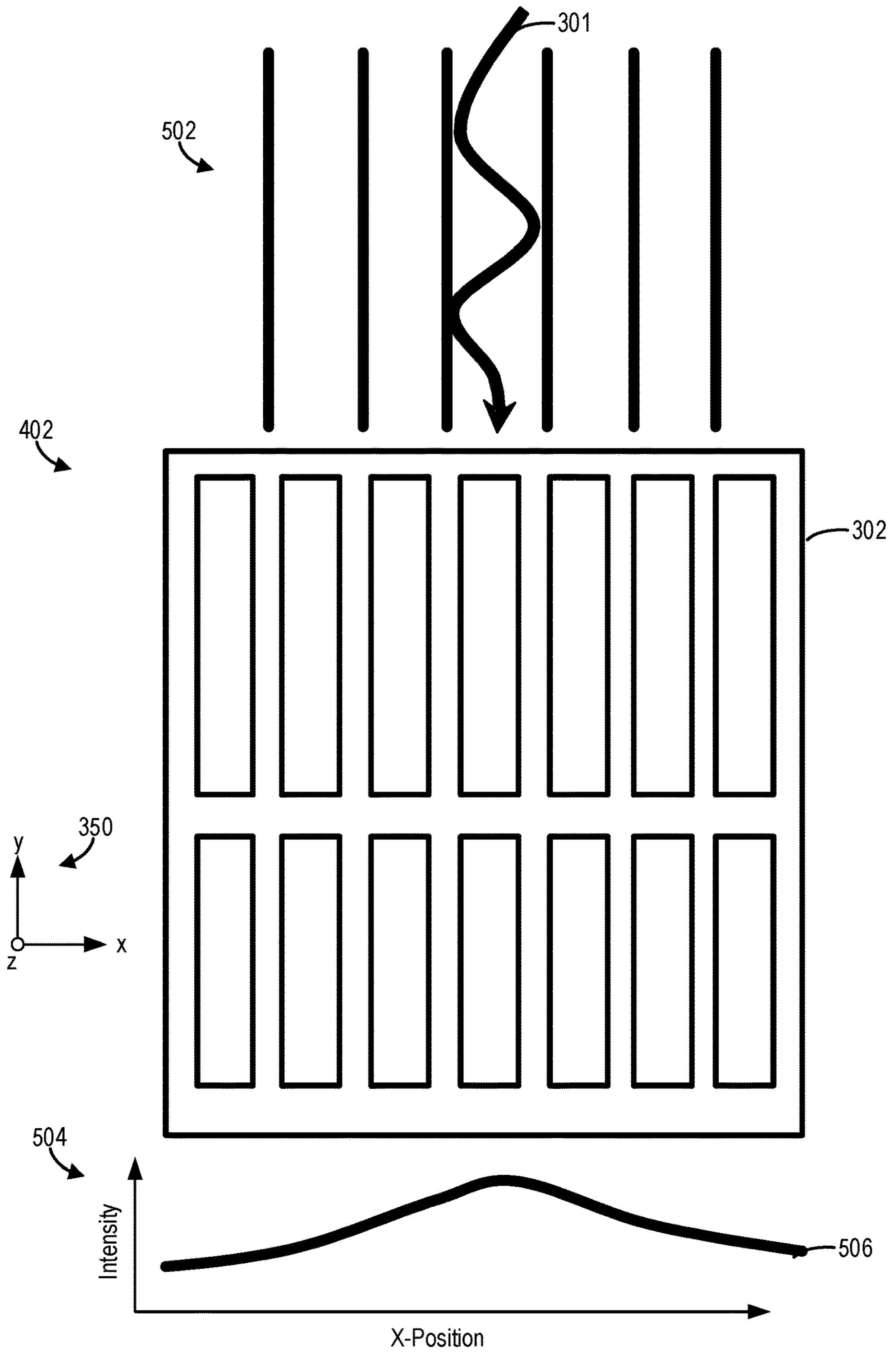
FIG. 5 shows a second perspective view of a sensor of the PCCT detector unit and related scattering.
Figure 10:
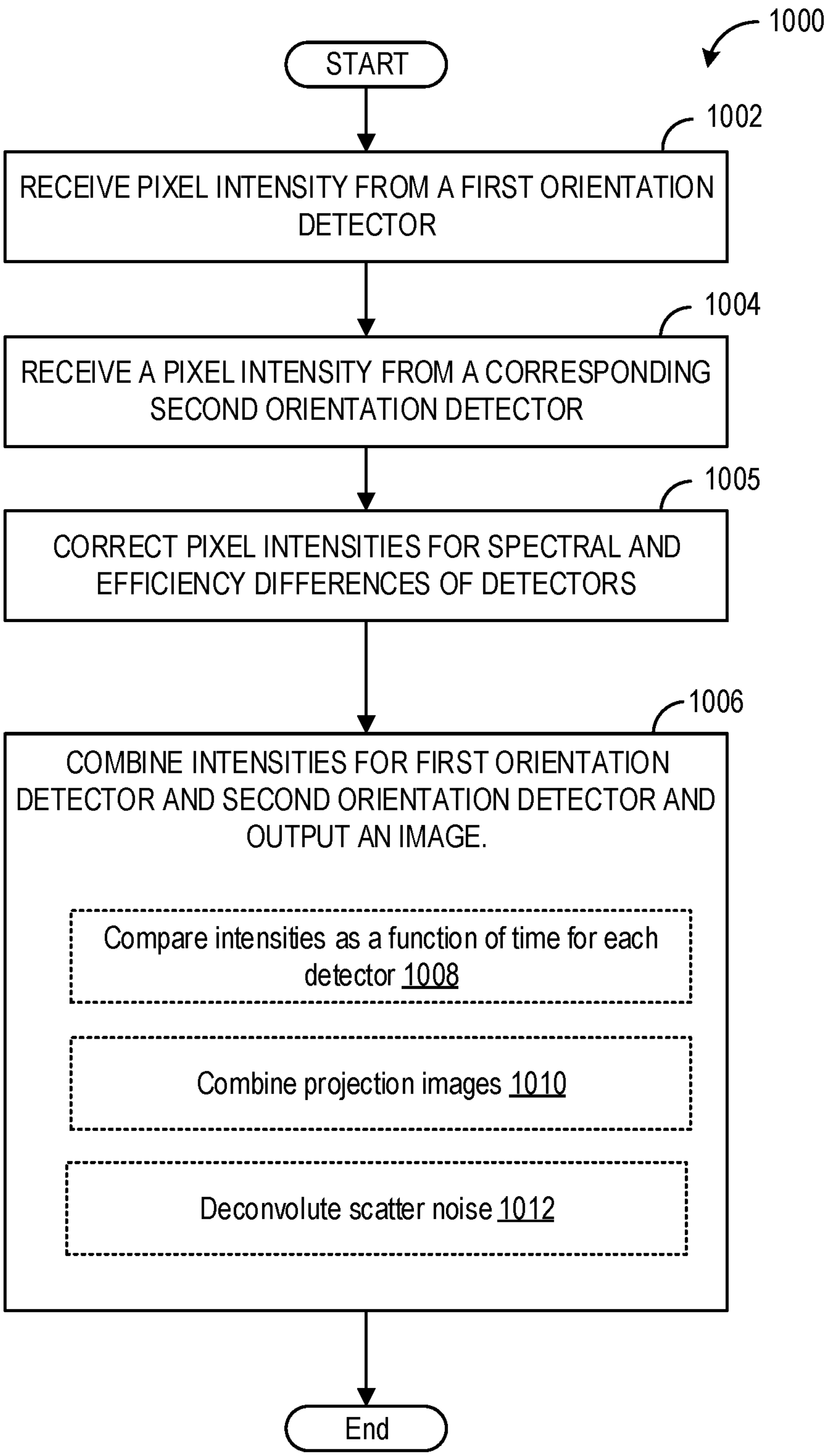
FIG. 10 shows a flowchart of an example of a method for correcting internal scatter of a PCCT detector array.
Figure 11:
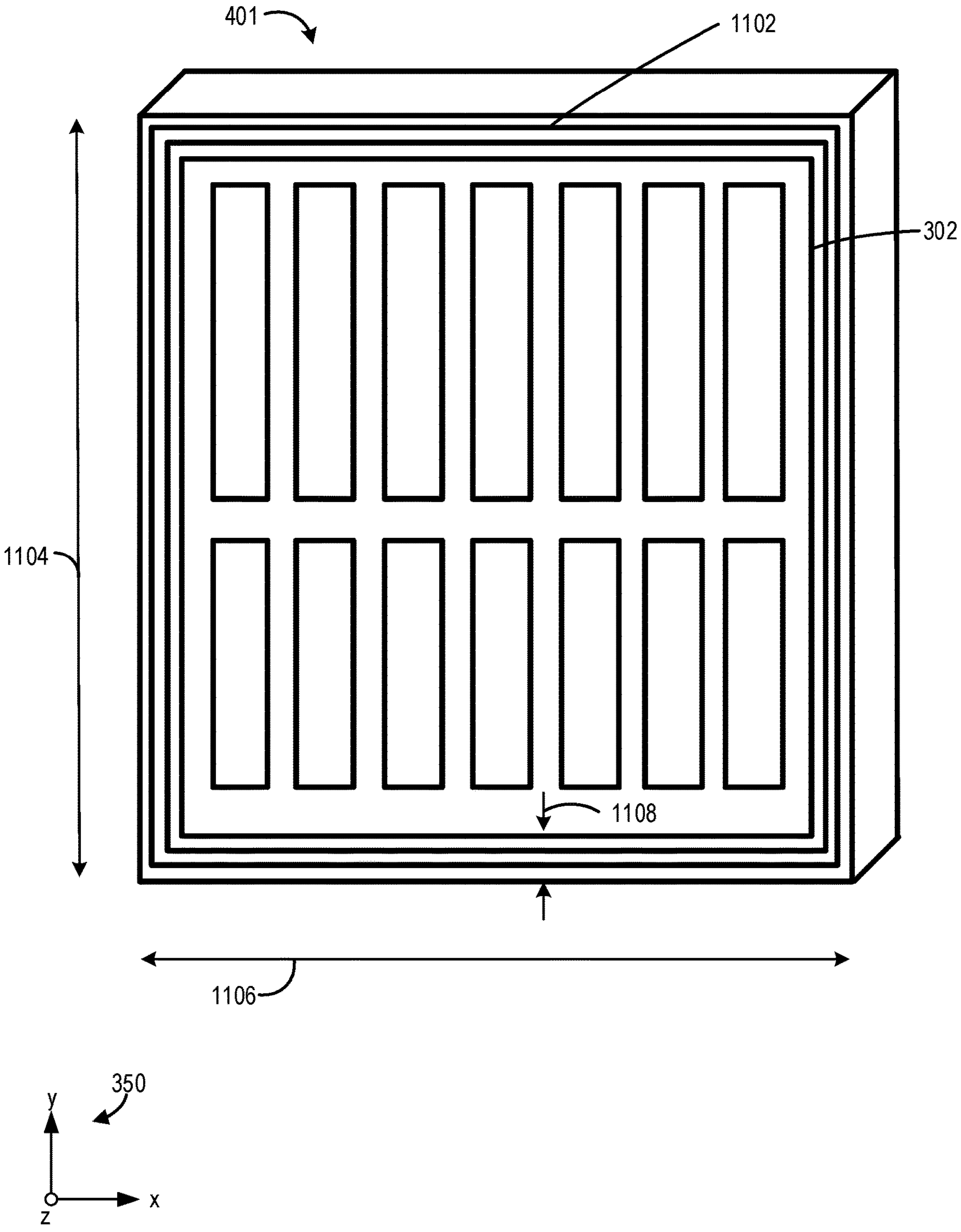
FIG. 11 shows a PCCT sensor stack with a guard ring.
Figure 12:
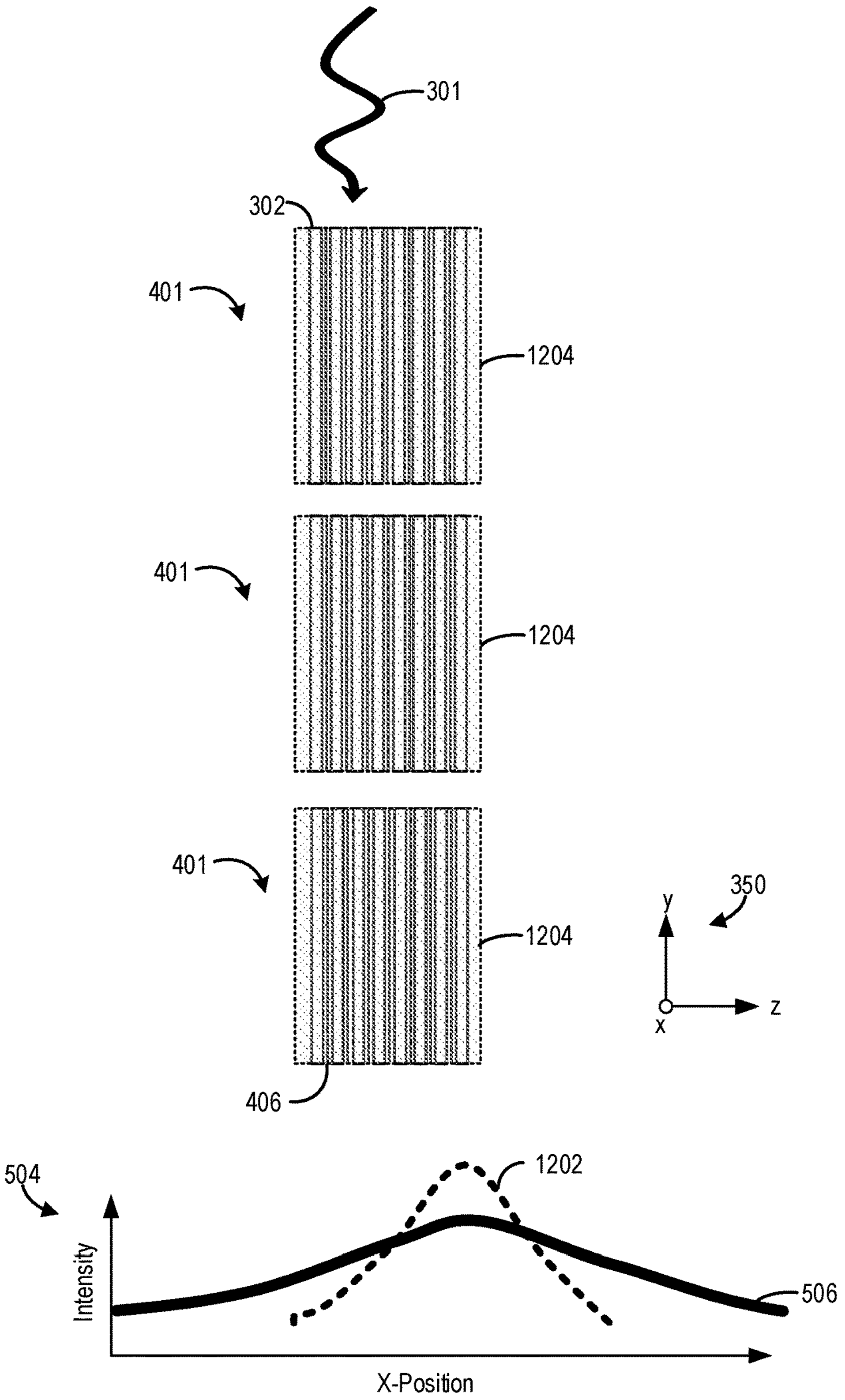
FIG. 12 shows PCCT sensor stacks.
Figure 13:
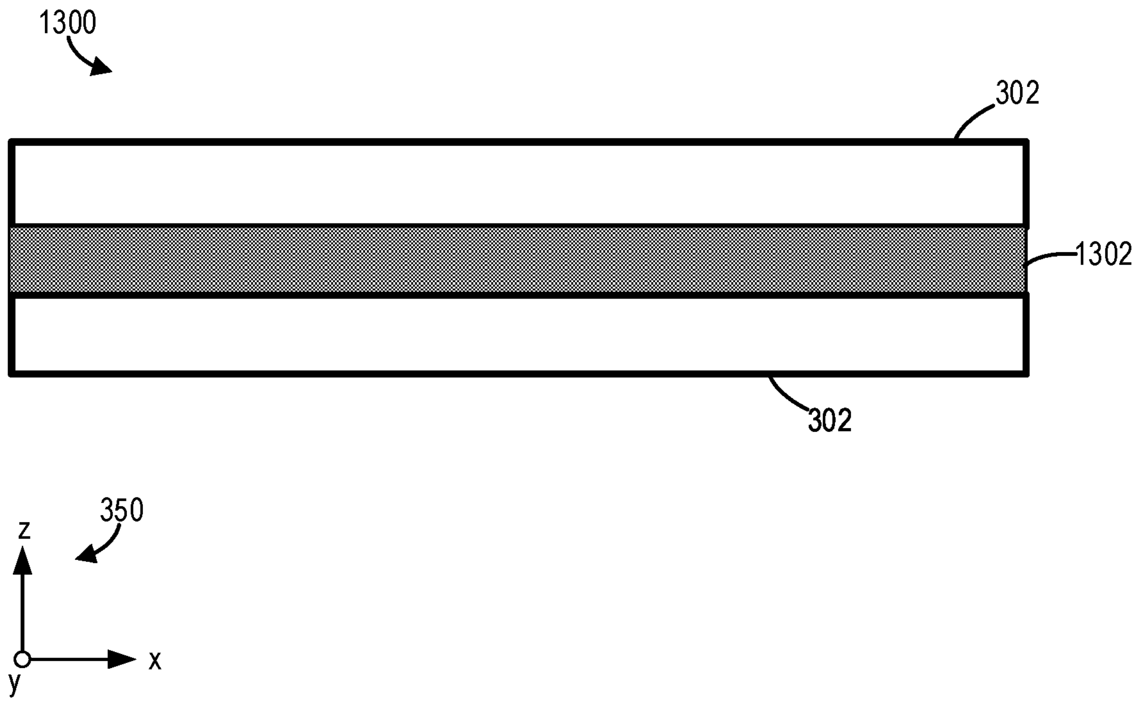
FIG. 13 shows a first perspective view of sensors of a PCCT detector unit including adhesive.
Figure 14:
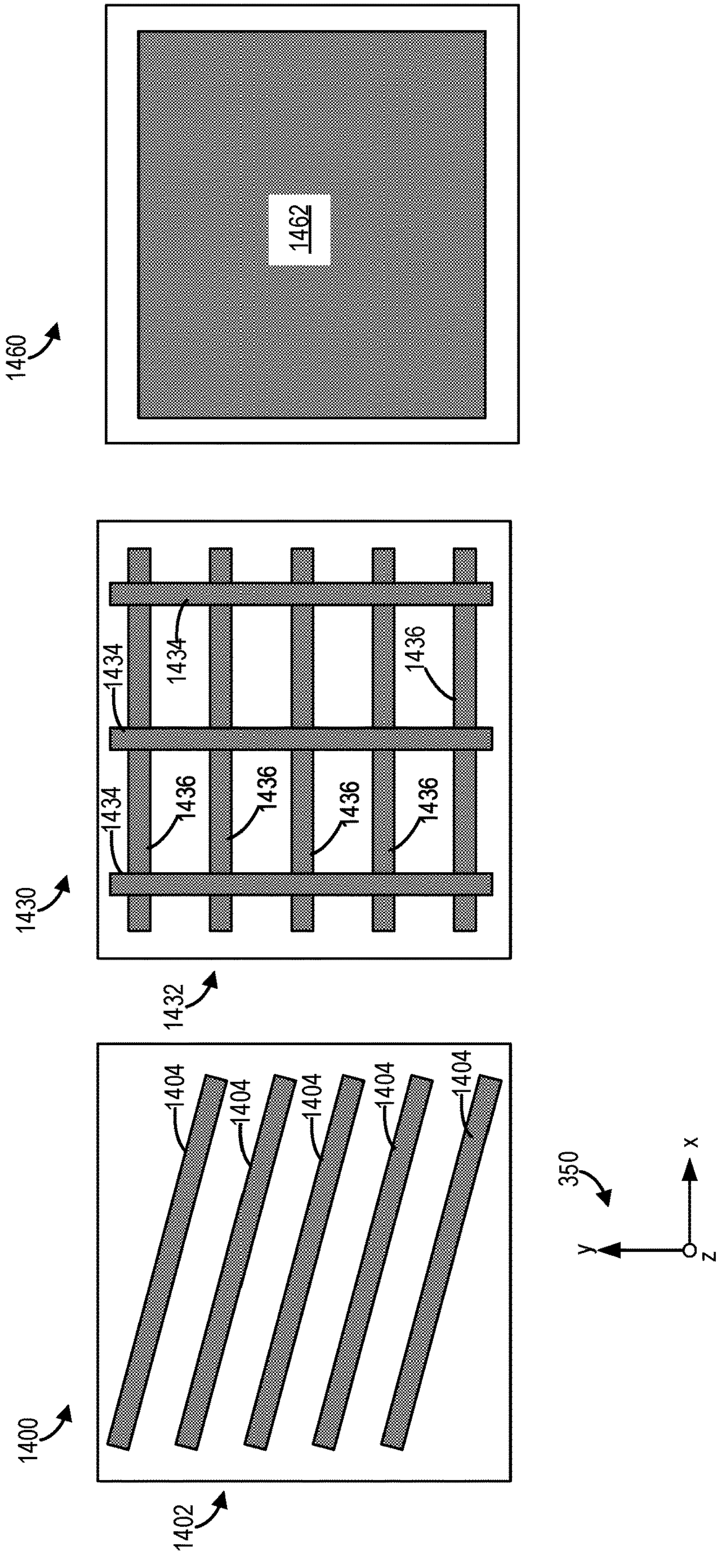
FIG. 14 shows a second perspective view of examples a sensor of the PCCT detector unit including adhesive.

The following description relates to systems and methods for correcting internal scatter of a photon-counting computed tomography (PCCT) detector unit. Computed tomography (CT) uses X-rays to probe a subject (e.g., a patient). Examples of a CT imaging system are shown in FIGS. 1-2. X-rays are scattered off of the subject and collected at an array of detectors positioned directly opposite the X-ray source. In some examples, the detectors may be conventional detectors which include a ceramic material and photodetectors, where energy from the X-rays causes emission of lower energy photons from the ceramic material. The lower energy photons are then converted to electrical signals by the photodetectors, and the electrical signals are used to form an image. An increase in image quality may be achieved by using a photon-counting detector which includes a semiconductor configured to absorb and convert energy from the scattered X-rays directly into electrical signals. A common source of noise in PCCT detector units are electrical signals that are due to further scattering of X-rays between and within sensors of the PCCT detector unit. An example of a sensor of a PCCT detector unit is shown in FIG. 3. X-ray scatter between sensors of the PCCT detector unit may be suppressed by an anti-scatter grid positioned between sensors of a PCCT detector unit as shown in FIG. 4. However, subunits of the sensor may still be subject to internal scatter between subunits as shown in FIG. 5. As one example, an array of PCCT detector units may be adapted to allow internal scattering crosstalk to be corrected by an image processing system. Examples of embodiments of the array of PCCT detectors is shown in FIGS. 6-9. An example of a flowchart of a method for decreasing the internal scattering crosstalk using the arrays of PCCT detector units of FIGS. 6-9 is shown in FIG. 10. Additionally or alternatively, PCCT detector units may be constructed to further decrease occurrence of internal scatter by adding foil of X-ray absorbing material as shown in FIGS. 11-12, and/or by strategies of reducing a solid angle of the scattered X-rays, such as with the addition of adhesives and/or X-ray absorbing material is shown in FIGS. 13-14. Further, PCCT detector units may internally incorporate X-ray absorbing material as trenches separating one or more pixels of a sensor. Examples of sensors including trenches are shown in FIGS. 15-18.

Turning now to FIG. 1, it illustrates an exemplary CT system 100 configured for CT imaging. Particularly, the CT system 100 is configured to image a subject 112 such as a patient, an inanimate object, one or more manufactured parts, and/or foreign objects such as dental implants, stents, and/or contrast agents present within the body. In one embodiment, the CT system 100 includes a gantry 102, which in turn, may further include at least one X-ray source 104 configured to project a beam of X-ray radiation 106 (see FIG. 2) for use in imaging the subject 112 laying on a table 114. Specifically, the X-ray source 104 is configured to project the X-ray radiation beams 106 towards a detector array 108 positioned on the opposite side of the gantry 102. Although FIG. 1 depicts a single X-ray source 104, in certain embodiments, multiple X-ray sources and detectors may be employed to project a plurality of X-ray radiation beams for acquiring projection data at different energy levels corresponding to the patient. In some embodiments, the X-ray source 104 may enable dual-energy gemstone spectral imaging (GSI) by rapid peak kilovoltage (kVp) switching. In some embodiments, the X-ray detector employed is a photon-counting detector which is capable of differentiating X-ray photons of different energies. In other embodiments, two sets of X-ray sources and detectors are used to generate dual-energy projections, with one set at low-kVp and the other at high-kVp. It should thus be appreciated that the methods described herein may be implemented with single energy acquisition techniques as well as dual energy acquisition techniques.

In certain embodiments, the CT system 100 further includes an image processor unit 110 including one or more processors configured to reconstruct images of a target volume of the subject 112 using an iterative or analytic image reconstruction method. For example, the image processor unit 110 may use an analytic image reconstruction approach such as filtered back projection (FBP) to reconstruct images of a target volume of the patient. As another example, the image processor unit 110 may use an iterative image reconstruction approach such as advanced statistical iterative reconstruction (ASIR), conjugate gradient (CG), maximum likelihood expectation maximization (MLEM), model-based iterative reconstruction (MBIR), and so on to reconstruct images of a target volume of the subject 112. As described further herein, in some examples the image processor unit 110 may use an analytic image reconstruction approach such as FBP in addition to an iterative image reconstruction approach.

In some CT imaging system configurations, an X-ray source projects a cone-shaped X-ray radiation beam which is collimated to lie within an X-Y-Z plane of a Cartesian coordinate system and generally referred to as an "imaging plane." The X-ray radiation beam passes through an object being imaged, such as the patient or subject. The X-ray radiation beam, after being attenuated by the object, impinges upon an array of detector elements. The intensity of the attenuated X-ray radiation beam received at the detector array is dependent upon the attenuation of an X-ray radiation beam by the object. Each detector element of the array produces a separate electrical signal that is a measurement of the X-ray beam attenuation at the detector location. The attenuation measurements from all the detector elements are acquired separately to produce a transmission profile.

In some CT systems, the X-ray source and the detector array are rotated with a gantry within the imaging plane and around the object to be imaged such that an angle at which the X-ray beam intersects the object constantly changes. A group of X-ray radiation attenuation measurements, e.g., projection data, from the detector array at one gantry angle is referred to as a "view." A "scan" of the object includes a set of views made at different gantry angles, or view angles, during one revolution of the X-ray source and detector.

The X-ray source 104 includes an anode and a cathode. Electrons emitted by the cathode (e.g., resulting from energization of the cathode) may be intercepted by a target arranged at or near the anode. Electrons intercepted by the target may release energy in the form of X-rays, with the X-rays being directed toward the detector array 108. An area of the target surface that receives the electrons from the cathode and forms the emitted X-rays may be referred to herein as a "focal spot." The emitted X-rays may be focused on a portion of the scanned subject 204, at an "effective focal spot". A size of the effective focal spot may depend on an angle of the actual focal spot (e.g., on the target surface). For example, a small effective focal spot may be desirable when scanning a small area, while a large effective focal spot may be desirable when scanning a larger area.

In some embodiments, an X-ray generation system including the X-ray source 104 may move and/or shape the focal spot. For example, the X-ray generation system may increase or decrease a size of the focal spot. Additionally, in some embodiments, the X-ray generation system may generate a composite focal spot, where the composite focal spot is a combination of two or more discrete focal spots. For example, two discrete focal spots located apart from each other may be combined to produce a single, composite focal spot.

FIG. 2 illustrates an exemplary imaging system 200 similar to the CT system 100 of FIG. 1. In accordance with aspects of the present disclosure, the imaging system 200 is configured for imaging a subject 204 (e.g., the subject 112 of FIG. 1). In one embodiment, the imaging system 200 includes the detector array 108 (see FIG. 1). The detector array 108 further includes a plurality of detector units 202 that together sense the X-ray radiation beam 106 (see FIG. 1) that pass through the subject 204 (such as a patient) to acquire corresponding projection data. In some embodiments, the detector array 108 may be fabricated in a multi-slice configuration including the plurality of detector units 202, where one or more additional rows of the detector units 202 are arranged in a parallel configuration for acquiring the projection data. In an exemplary embodiment, detector units 202 may be PCCT detector units arranged as described further below with respect to FIGS. 6-9. Such arrangements may allow correction for internal scattering crosstalk in CT images.

In certain embodiments, the imaging system 200 is configured to traverse different angular positions around the subject 204 for acquiring desired projection data. Accordingly, the gantry 102 and the components mounted thereon may be configured to rotate about a center of rotation 206 for acquiring the projection data, for example, at different energy levels. Alternatively, in embodiments where a projection angle relative to the subject 204 varies as a function of time, the mounted components may be configured to move along a general curve rather than along a segment of a circle.

As the X-ray source 104 and the detector array 108 rotate, the detector array 108 collects data of the attenuated X-ray beams. The data collected by the detector array 108 undergoes pre-processing and calibration to condition the data to represent the line integrals of the attenuation coefficients of the scanned subject 204. The processed data are commonly called projections. In some examples, the individual detectors or detector units 202 of the detector array 108 may include photon-counting detectors which register the interactions of individual photons into one or more energy bins. It should be appreciated that the methods described herein may also be implemented with energy-integrating detectors.

The acquired sets of projection data may be used for basis material decomposition (BMD). During BMD, the measured projections are converted to a set of material-density projections. The material-density projections may be reconstructed to form a pair or a set of material-density map or image of each respective basis material, such as bone, soft tissue, and/or contrast agent maps. The density maps or images may be, in turn, associated to form a 3D volumetric image of the basis material, for example, bone, soft tissue, and/or contrast agent, in the imaged volume.

Once reconstructed, the basis material image produced by the imaging system 200 reveals internal features of the subject 204, expressed in the densities of two or more basis materials. The density image may be displayed to show these features. In traditional approaches to diagnosis of medical conditions, such as disease states, and more generally of medical events, a radiologist or physician would consider a hard copy or display of the density image to discern characteristic features of interest. Such features might include lesions, sizes and shapes of particular anatomies or organs, and other features that would be discernable in the image based upon the skill and knowledge of the individual practitioner.

In one embodiment, the imaging system 200 includes a control mechanism 208 to control movement of the components such as rotation of the gantry 102 and the operation of the X-ray source 104. In certain embodiments, the control mechanism 208 further includes an X-ray controller 210 configured to provide power and timing signals to the X-ray source 104. Additionally, the control mechanism 208 includes a gantry motor controller 212 configured to control a rotational speed and/or position of the gantry 102 based on imaging requirements.

In certain embodiments, the control mechanism 208 further includes a data acquisition system (DAS) 214 configured to sample analog data received from the detector elements 202 and convert the analog data to digital signals for subsequent processing. The data sampled and digitized by the DAS 214 is transmitted to a computer or computing device 216 including one or more processors. In one example, the computing device 216 stores the data in a storage device or mass storage 218. The storage device 218, for example, may be any type of non-transitory memory and may include a hard disk drive, a floppy disk drive, a compact disk-read/write (CD-R/W) drive, a Digital Versatile Disc (DVD) drive, a flash drive, and/or a solid-state storage drive.

Additionally, the computing device 216 provides commands and parameters to one or more of the DAS 214, the X-ray controller 210, and the gantry motor controller 212 for controlling system operations such as data acquisition and/or processing. In certain embodiments, the computing device 216 controls system operations based on operator input. The computing device 216 receives the operator input, for example, including commands and/or scanning parameters via an operator console 220 operatively coupled to the computing device 216. The operator console 220 may include a keyboard (not shown) or a touchscreen to allow the operator to specify the commands and/or scanning parameters.

Although FIG. 2 illustrates one operator console 220, more than one operator console may be coupled to the imaging system 200, for example, for inputting or outputting system parameters, requesting examinations, plotting data, and/or viewing images. Further, in certain embodiments, the imaging system 200 may be coupled to multiple displays, printers, workstations, and/or similar devices located either locally or remotely, for example, within an institution or hospital, or in an entirely different location via one or more configurable wired and/or wireless networks such as the Internet and/or virtual private networks, wireless telephone networks, wireless local area networks, wired local area networks, wireless wide area networks, wired wide area networks, etc.

In one embodiment, for example, the imaging system 200 either includes, or is coupled to, a picture archiving and communications system (PACS) 224. In an exemplary implementation, the PACS 224 is further coupled to a remote system such as a radiology department information system, hospital information system, and/or to an internal or external network (not shown) to allow operators at different locations to supply commands and parameters and/or gain access to the image data.

The computing device 216 uses the operator-supplied and/or system-defined commands and parameters to operate a table motor controller 226, which in turn, may control a table 114 which may be a motorized table. Specifically, the table motor controller 226 may move the table 114 for appropriately positioning the subject 204 in the gantry 102 for acquiring projection data corresponding to the target volume of the subject 204.

As previously noted, the DAS 214 samples and digitizes the projection data acquired by the detector units 202. Subsequently, an image reconstructor 230 uses the sampled and digitized X-ray data to perform high-speed reconstruction. Although FIG. 2 illustrates the image reconstructor 230 as a separate entity, in certain embodiments, the image reconstructor 230 may form part of the computing device 216. Alternatively, the image reconstructor 230 may be absent from the imaging system 200 and instead the computing device 216 may perform one or more functions of the image reconstructor 230. Moreover, the image reconstructor 230 may be located locally or remotely, and may be operatively connected to the imaging system 200 using a wired or wireless network. Particularly, one exemplary embodiment may use computing resources in a “cloud” network cluster for the image reconstructor 230.

In one embodiment, the image reconstructor 230 stores the images reconstructed in the storage device 218. Alternatively, the image reconstructor 230 may transmit the reconstructed images to the computing device 216 for generating useful patient information for diagnosis and evaluation. In certain embodiments, the computing device 216 may transmit the reconstructed images and/or the patient information to a display or display device 232 communicatively coupled to the computing device 216 and/or the image reconstructor 230. In some embodiments, the reconstructed images may be transmitted from the computing device 216 or the image reconstructor 230 to the storage device 218 for short-term or long-term storage.

Referring now to FIG. 3, a partial view of a photon-counting detector element 300 of a PCCT detector unit is shown. Reference axes 350 are provided including an x-axis, y-axis, and z-axis. Reference axes 350 are used to compare views of the portions of PCCT detector unit shown in the views of FIGS. 3-5, 11, and 12. Photon-counting detector element 300 may be a non-limiting embodiment of a detector element of detector unit 202 of FIG. 2, where a plurality of rows of detector elements 300 may be arranged in a parallel configuration stacked along a stacking direction 320 parallel with the z-axis to form a detector unit (e.g., detector array 108) for acquiring the projection data, as described above.

Photon-counting detector element 300 includes a sensor 302, which may be electronically coupled to a printed circuit board (PCB) 316. PCB 316 includes a connection 318 to readout electronics of the detector element 300. An application-specific integrated circuit (ASIC) 312 may be mounted on PCB 316, which, along with the readout electronics, forms part of a DAS of the PCCT system (e.g., DAS 214).

In various embodiments, sensor 302 may be embedded in a chip made of a semi-conductor material, such as silicon. A width of the chip (e.g., along the z-axis) may be one pixel at an edge 311 of sensor 302. A plurality of sensors may be embedded along a surface of the chip and extending along a length of the chip. Sensor 302 may be configured to count photons impacting edge 311 of sensor 302. Specifically, for each pixel (e.g., subsensor) 309 along edge 311, one or more sensor segments 305 may be embedded in a column 303 extending below each pixel 309, oriented in a direction 307 of incoming X-ray beams 301 (e.g., vertically in FIG. 3). Each sensor segment 305 of each column 303 may have a width across the surface of sensor 302 of approximately one pixel, corresponding to a pixel 309 at edge 311 corresponding to a relevant column 303. Each sensor segment 305 of each column 303 may count a number of photons of an incoming X-ray beam 301 impacting edge 311 at a corresponding pixel 309.

In other words, each column 303 may include a plurality of sensor segments 305 stacked vertically in the column 303 in the direction 307. For example, each (vertically depicted) column 303 may include a first segment at a first vertical position 304; a second segment at a second vertical position 306, and so on. In the embodiment depicted in FIG. 3, each column 303 includes two of sensor segments 305. In other embodiments, each column 303 may include three, four, or a different number of segments 305. A size of each segment 305 in a column 303 may be the same, or each segment 305 in a column 303 may be different. For example, a first segment 305 of a column 303 may be larger than a second segment 305 of the column 303. A third segment 305 of the column 303 may be smaller than the second segment 305 of the column 303.

Each segment 305 may be electrically coupled to ASIC 312 mounted on PCB 316. In various embodiments, each segment 305 of sensor 302 may be electrically coupled to a sensor bond pad 310 of sensor 302 via a PCCT sensor trace 308. Sensor bond pad 310 may be electrically coupled to ASIC 312 via a wire bond 314.

Each segment 305 may detect a number of incoming photons in an X-ray beam 301. As the X-ray beam 301 impacts sensor 302 at a pixel 309, the X-ray beam 301 may pass through a plurality of segments 305 that are stacked (e.g., vertically arranged) in a corresponding column 303. As the X-ray beam 301 passes through each segment 305 of the column 303, a number of photons included in the X-ray beam 301 may be detected at the segment 305.

For example, an exemplary X-ray beam 301 may enter a first segment 305 in the first vertical position 304 of the column 303, and the first segment 305 may detect a first number of photons of the exemplary X-ray beam 301. The first number of photons may be less than a total number of photons of the exemplary X-ray beam 301, where a second number of the total number of photons may pass through the first segment 305 undetected. The second number of (undetected) photons of the exemplary X-ray beam 301 passing through the first segment 305 may then enter a second segment 305 at the second vertical position 306 of the column 303. The second segment 305 may detect a third number of photons of the exemplary X-ray beam 301. The third number of photons may be less than the second number of photons, where a fourth number of photons may pass through the second segment 305 undetected. The fourth number of photons of the exemplary X-ray beam 301 passing through the second segment 305 may then enter a third segment 305 at a third vertical position of the column 303, and so on. Thus, the total number of detected photons of the exemplary X-ray beam 301 may be estimated by summing the number of photons detected by each vertically stacked segment 305 of the column 303.

The number of photons detected at each vertically stacked segment 305 of the column 303 may vary. For example, in some cases, all of the photons in the exemplary X-ray beam 301 may be detected by the first segment 305, and none of the photons in exemplary X-ray beam 301 may be detected by the second segment 305. In other cases, a large percentage of the photons in the exemplary X-ray beam 301 may be detected by the first segment 305, and a smaller percentage of the photons in exemplary X-ray beam 301 may be detected at the second segment 305, an even smaller percentage of the photons in exemplary X-ray beam 301 may be detected at the third segment 305, and so on. Some photons of the exemplary X-ray beam 301 may not be detected at any of the segments 305 of the column 303, where the total number of detected photons may not be equal to the total number of photons of the exemplary X-ray beam 301.

When a photon hits a segment 305, an analog electrical signal is generated that is transmitted to ASIC 312 via sensor trace 308 and sensor bond pad 310, where the analog electrical signal is proportional to an amount of energy of the photon. ASIC 312 may convert the analog electrical signal to a digital signal by counting the occurrence of the photon hit in a counter. Furthermore, ASIC 312 may discern the energy deposited by the photon by comparing the amount of electrical signal to one or more pre-established thresholds. Specifically, ASIC 312 may include a plurality of comparators, where each comparator of the plurality of comparators outputs a trigger signal that causes a corresponding digital counter to increment by one when the analog signal exceeds a signal level threshold associated with the comparator. Each comparator of the plurality of comparators may have a different signal level threshold. For example, ASIC 312 may include a first comparator with a first signal level threshold; a second comparator with a second signal level threshold, the second signal level threshold higher than the first signal level threshold; a third comparator with a third signal level threshold, the third signal level threshold higher than the second signal level threshold; and so on, up to a maximum energy level of a spectrum of photons. The differences between pairs of thresholds define energy ranges or bins. Thus, the number of photons whose energies fall within each bin may be recorded by the ASIC 312. These numbers of photon counts may be transmitted by the ASIC 312 to the PCB 316 via connection 318 to be used for image reconstruction. Alternatively, the ASIC 312 may first perform additional operations on the numerical count information, such as summing together the individual photon counts from the bins within a given column to produce a total number of photon counts.

Noise of a PCCT detected image may result from photons impinging on sensor 302 which have not interacted with the object being imaged or which have interacted with other components of the CT imaging system before reaching sensor 302. For example, instead of being absorbed by sensor 302, photons may scatter off of sensor 302 and be absorbed by a neighboring sensor of the PCCT detector unit. An anti-scatter grid may prevent intersensor scattering crosstalk as shown in FIG. 4.

Turning now to FIG. 4, it shows a side view of PCCT detector unit 402 viewed along the x-axis. PCCT detector unit 402 may include a plurality of sensors 302 stacked along stacking direction 320. Sensors 302 may each be included in a sensing element, such as photon-counting detector element 300. FIG. 4 shows the sensor 302 and omits other components of sensing element 300 for clarity. An anti-scatter grid 404 includes a plurality of fins 406. Each fin of the plurality of fins 406 may be interposed between two adjacent sensors 302 in stacking direction 320. Fins 406 may extend to a height along the y-axis at least equivalent to a height of sensors 302 along the y-axis. In some examples, a thickness of fins 406 along the stacking direction may be less than thickness of sensors 302 along the stacking direction, however other relative thickness of fins 406 and sensors 302 are also considered. Fins 406 may be formed of a metal or metal alloy capable of absorbing scattered X-ray photons. For example, fins 406 may comprise sheets of tungsten (W) or tungsten alloy. Further, fins 406 may be adhered to sensors 302 by epoxy interposed between fins 406 and sensors 302. In this way, X-rays scattered off of one sensor 302 are absorbed by an intervening fin of anti-scatter grid 404 and do not reach the adjacent fin. A sensor stack 401 may comprise a plurality of sensors 302 and a plurality of fins 406, wherein the fins 406 are interposed between the sensors 302.

A graph 408 shows intensity as a function of position along the z-axis. A value along the x-axis of graph 408 corresponds with the illustration of PCCT detector unit 402. A plot 410 shows a peak corresponding to an incoming X-ray beam 301, shown as an arrow. The incoming X-ray may interact with one sensor 302. Any scattering off of the one sensor 302 to adjacent sensors is substantially absorbed by intervening fins 406 and a signal intensity is not registered at adjacent sensors. For this reason, plot 410 shows a peak with a peak width roughly equivalent to a width of one sensor 302. It is noted that plot 410 is an approximation of the signal intensity and secondary peaks may still occur in the z-direction, even with fins 406 blocking a majority of the X-rays scattered in the Z-direction. Further, the peak width may not be greater than the width of one sensor 302.

Turning now to FIG. 5, it shows a side view of PCCT detector unit 402 along the stacking axis (e.g., the z-axis). Viewed along the stacking axis, a face in the x-y plane of one sensor 302 is shown including pixels arranged in columns and each pixel including sub-sensors. FIG. 5 also shows a collimator 502. The collimator may be positioned in front of PCCT detector unit 402, between the object being imaged and PCCT detector unit 402. The incoming X-ray beam 301 may interact with collimator before reaching PCCT detector unit 402. Collimator 502 directs divergent X-ray scatter from the object in a single direction towards PCCT detector unit 402. In this way, X-ray scatter may be reduced by the collimator before reaching the PCCT detector unit 402. However, within each sensor 302, scattering may not be prevented in the x-direction.

The X-ray may interact with a pixel of sensor 302. A graph 504 shows intensity as a function of position along the x-axis of sensor 302. A plot 506 shows a peak aligned with the pixel which absorbed the incoming X-ray. Plot 506 is a broad distribution of intensities around the peak, corresponding to intensities registered at pixels neighboring the pixel which interacted with X-ray. The intensity in neighboring pixels may be caused by scattering of the X-ray internal to sensor 302. The broad curve of plot 506 may be a source of noise and may decrease a resolution of a collected image, and additionally may cause spectral corruption resulting contamination of material images (e.g., mixing of any one of the materials in the other material images and so on).

The internal scattering shown in FIG. 5 may not be mitigated by the anti-scattering grid shown in FIG. 4, which merely blocks scattering between sensors and does not block scattering within each sensor. Thus, scattering may be allowed in one of the orthogonal directions to the X-ray. For example, scattering of the X-ray traveling in the y-direction to the PCCT detector unit 402 may be reduced in the z-direction, but not in the x-direction. Therefore, a resolution of the resulting image may not be adequate due to X-ray scattering in the x-direction. Without further modifying PCCT detector unit 402, an arrangement of PCCT detector units 402 in an array may be strategically adapted (e.g., arranged) to determine which signals are due to internal scattering so that such signals may be removed from the image by an image processing system.

As described above with respect to FIG. 2, a plurality of PCCT detector units may be arranged in an arc around a circumference of the gantry. Conventionally, PCCT detector units may each be positioned with a stacking axis of the PCCT detector unit positioned parallel with an axis of rotation of the gantry. FIGS. 6-9 show embodiments including at least one of the PCCT detector units positioned with the stacking axis positioned at least partially tangent to a circumference of the gantry and at an angle with respect to the axis of rotation of the gantry.

Figure 6:
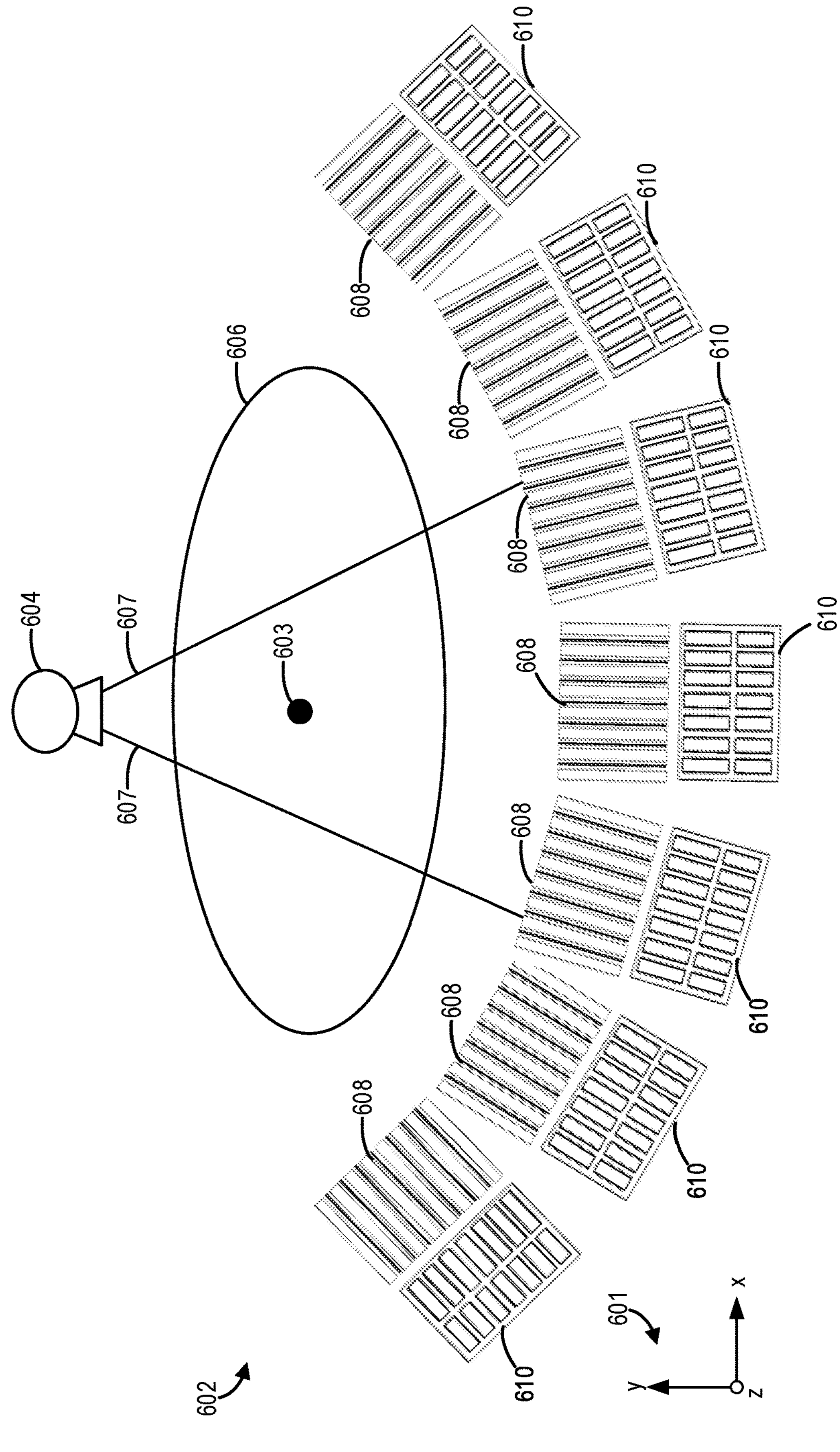
FIG. 6 shows a diagram of a first embodiment of an array of PCCT detector units.

A first embodiment 602 of a detector array is shown schematically in FIG. 6. FIG. 6 also shows a position of an X-ray source 604 and an object 606 being imaged. The detector array of FIGS. 6-9 may be examples of a detector array included in a computed tomography system, such as CT system 100 of FIGS. 1-2. In some examples, object 606 may be a patient. Reference axes 601, including an x-axis, y-axis and z-axis, are provided for comparison between the embodiments shown in FIGS. 6-9. X-rays 607 may be emitted from X-ray source 604 in an imaging direction parallel with the y-axis. Emitted X-rays may radiate outwards from the X-ray source 604 in the imaging direction and interact with object 606 before impinging on detector array 602. X-ray source 604 and the detector array 602 may each be rotated by the gantry (omitted for clarity) around the object and around an axis of rotation parallel with the axis and indicated by point 603.

The detector array 602 may include a plurality of horizontally oriented PCCT detector units 608 and a plurality of vertically oriented PCCT detector units 610. For example, there may be a same number of horizontally oriented PCCT detector units 608 as vertically oriented PCCT detector units 610. Horizontally oriented PCCT detector units 608 may be oriented with the stacking axis of the PCCT detector unit (e.g., the PCCT detector unit 402 of FIGS. 4 and 5)

positioned horizontally with respect to the object 606 and at an angle with respect to the axis of rotation. For example, horizontally oriented PCCT detector units 608 may be oriented with a stacking axis perpendicular to the axis of rotation. Vertically oriented PCCT detector units 610 may be oriented with the stacking axis of the PCCT detector unit (e.g., the PCCT detector unit 402 of FIGS. 4 and 5) vertical with respect to object 606 and parallel to the axis of rotation. Vertically oriented PCCT detector units 610 may be rotated 90° with respect to the imaging axis with respect to horizontally oriented PCCT detector units 608. In this way a stacking axis of vertically oriented PCCT detector units 610 may be perpendicular to the stacking axis of horizontally oriented PCCT detector units 608.

At each detection angle, scattered X-rays may be detected by both the vertically oriented PCCT detector units 610 and the horizontally oriented PCCT detector unit 608, in contrast with current configurations which may include a single row of vertically oriented PCCT detector units 610. FIG. 6 shows for a given detection angle a horizontally oriented PCCT detector unit 608 may be positioned closer to object 606 than the vertically oriented PCCT detector unit 610. In this way, incident X-rays at a given detection angle may reach and be detected by both vertically oriented detector units and horizontally oriented detector units. In alternate examples, the positions may be switched and vertically oriented PCCT detector unit 610 may be positioned closer to object 606 than horizontally oriented PCCT detector unit 608. In further examples, an orientation of the PCCT detector unit closest to object 606 may be alternated between vertical and horizontal. In such examples, the X-rays may be incident on and detected by both vertically oriented PCCT detector units 610 and the horizontally oriented PCCT detector units 608. Further, a collimator such as the collimator 502 of FIG. 5, may be positioned between the array 602 and the object 606. In this way, scattering of X-rays may be reduced prior to detection by the collimator, and may be further reduced by the perpendicular configuration of PCCT detector units in the array 602.

Scattering noise that is horizontal with respect to object 606 may be blocked by an anti-scattering grid of horizontally oriented PCCT detector unit 608. Scattering noise that is vertical with respect to object 606 may be blocked by an anti-scattering grid of vertically oriented PCCT detector unit 610. By including both orientations of detectors at each detecting angle, a combined image may be formed where signal that occurs on both orientations is considered real signal and any signal registered in one orientation is considered noise. The combined image may not include the noise signals, thus increasing resolution of the image.

In some examples, the high count rates may of X-ray photons striking the PCCT detector units may demand use of an alternative means of analyzing the acquired images. For example, a signal registered at each pixel of a sensor may be a convolution of a primary photon signal (e.g., resulting from scatter off of the imaging object) and those scattered off of neighboring pixels (e.g., noise). The convolution may extend in the Z-direction for horizontally oriented detector units 608 and in the X-direction for vertically oriented detector units 610. In some examples, the convolutions may be less computationally intense and/or more simple than those resulting from a conventional placement of vertically oriented sensors alone. A filter kernel for spectral deconvolution of scatter corrupted signal may be provided for outputting images with decreased noise. The filter kernels for vertically oriented detector units 610 and horizontally oriented detector units 608 may be constructed differently to account for both the direction of scattering and beam-hardening of the spectrum.

Further, with respect to beam hardening, image processing may adjust an image acquired by detector array 602 to account for lower energy X-rays being absorbed by the PCCT detector unit positioned closer to object 606 before reaching the PCCT detector unit positioned further from object 606. In this way, X-rays may be hardened by the PCCT detector unit closest to object 606 before reaching the PCCT detector unit furthest from object 606.

Figure 7:
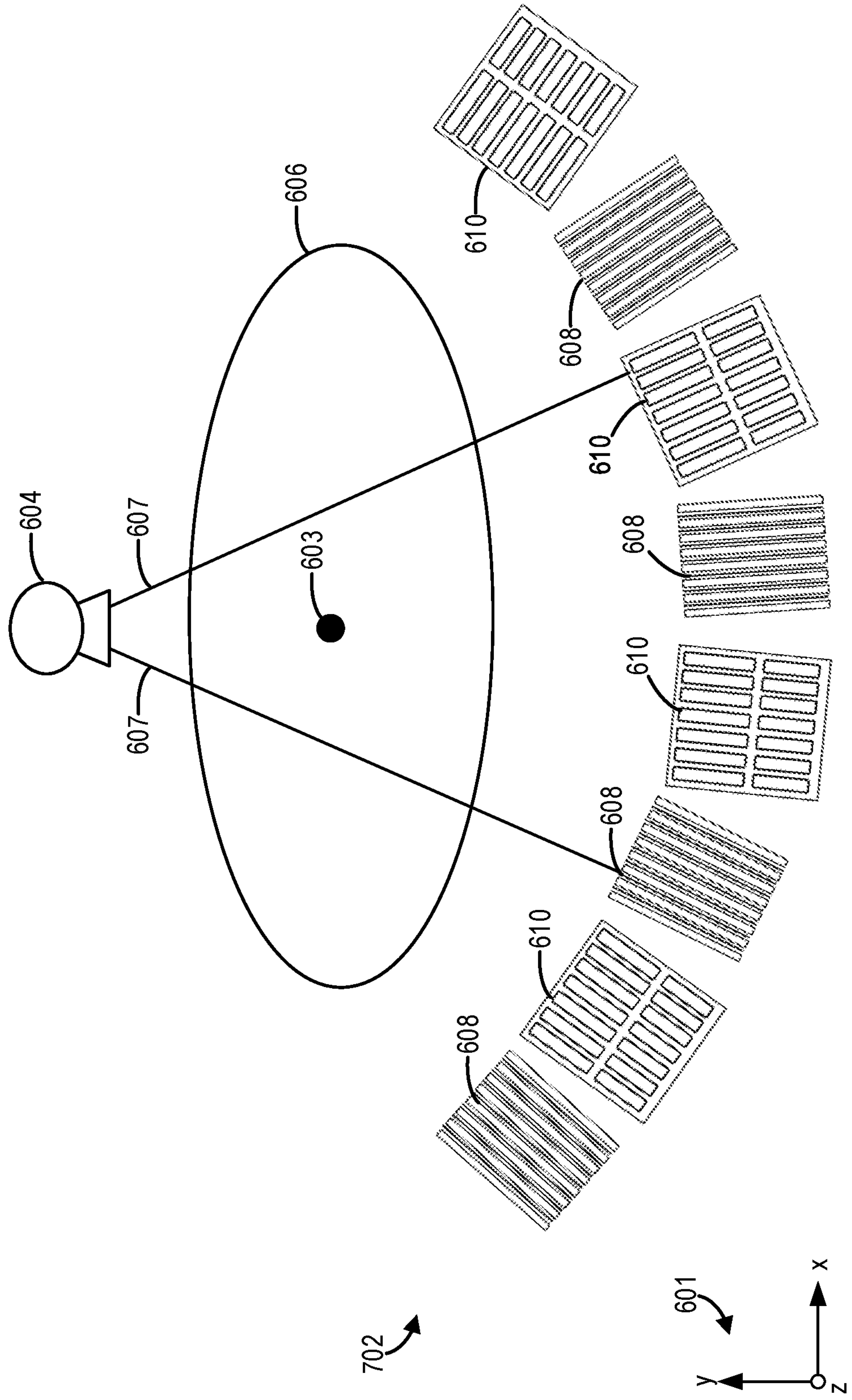
FIG. 7 shows a diagram of a second embodiment of an array of PCCT detector units.

As an alternate to adjusting for hardened X-rays, a detector array 702 shown in FIG. 7 may be used. The detector array 702 may include alternating horizontally oriented PCCT detector units 608 and vertically oriented PCCT detector units 610. The horizontally oriented PCCT detector units 608 and vertically oriented PCCT detector units 610 may be arranged approximately equidistantly from object 606. Further, collimators such as the collimator 502 of FIG. 5, may be positioned between the array 602 and the object 606. In this way, scattering of X-rays may be reduced by the collimators prior to detection, and may be further reduced by the configuration of PCCT detector units in the detector array 702. The single row arrangement may allow for scattered X-rays at a given detection angle to be detected by a single detector unit. Thus, the X-rays may be detected by a horizontally oriented detector unit or a vertically detector unit in such a configuration. For example, X-rays may be detected by either a horizontally oriented PCCT detector unit 608 or a vertically oriented PCCT detector unit 610. Further, the alternating pattern may allow for overall noise reduction in image processing. For example, by combining signals from the horizontally oriented PCCT detector units 608, a first image may be generated, and similarly, by combining signals from the vertically oriented PCCT detector units 610, a second image may be generated. The first image and the second image may have gaps in data due to the alternating arrangement. Thus, the first image and the second image may be incomplete as separate images. However, an image processing method may construct a continuous image from the first image and the second image. The construction of the continuous image may occur after images are corrected for spectral differences and for the convolution of scattering noise as described above. In examples where count rates are lower, the image processing method may further determine what signals may be noise from comparing the first image and the second image, and filter such signals out in order to produce a lower noise image. Further, for high count rate techniques, deconvolution techniques using filter kernels as described above may be used to correct for scatter noise.

Turning to FIG. 10, a flowchart of a method 1000 is shown for correcting internal scatter of a PCCT detector array including two different orientations of PCCT detectors units. For example, the method 1000 may be used to produce a higher resolution image from sensors of the detector arrays shown in FIGS. 6 and 7, wherein some of the PCCT detector units are horizontally oriented and some of the PCCT detector units are vertically oriented.

At 1002, the method 1000 includes receiving a first pixel intensity from a first orientation detector. For example, the first orientation detector may be a horizontally oriented detector, such as the horizontally oriented PCCT detector units 608 of FIGS. 6 and 7.

The method 1000 proceeds to 1004, wherein a second pixel intensity is received from a corresponding second orientation detector. For example, the second orientation detector may be a vertically oriented detector, such as the vertically oriented PCCT detector units 610 of FIGS. 6 and 7. Further, the corresponding second orientation detector may be adjacent to the first orientation detector. For example, the first and second orientation detectors may be aligned with a detection angle such that an X-ray may first pass through the first orientation detector and then through the second orientation detector as shown in FIG. 6. Alternatively, the first and second orientation detectors may be aligned side by side, such that the first orientation detectors may detect X-rays scatter at a different detection angle than the second orientation detectors.

At 1005, method 1000 includes correcting the pixel intensities for spectral and efficiency differences of the first orientation detectors and second orientation detectors. For example, correcting for spectral differences may include correcting for if the detector is preferentially exposed to harder or softer X-rays. As a further example, photon to electrical signal conversion efficiencies may be different between each PCCT detector unit, and the differences in efficiencies may be known (e.g., stored in a look-up table) and corrected for.

At 1006, method 1000 includes combining intensities for the first orientation detector and second orientation detector and outputting an image. By combining the intensities for the first orientation detector and the second orientation detector, a noise level of the combined image may be decreased compared to an image collected in a single orientation.

In examples where count rates are low, combining intensities for the first orientation detector and the second orientation may include, at 1008 comparing intensities at each the first orientation detector and second orientation detector as function of time. For example, an intensity at a pixel of the first orientation detector and a corresponding pixel of a second orientation detector may be compared. When it is determined that the pixel intensity of the first detector and the second detector match. Determining a match may include if the intensities are within a threshold difference (e.g., tolerance), the computing device may determine that the pixel intensities match. The threshold difference may be predetermined and programmed into the computing device. If it is determined that the pixel intensities match the pixel intensity is maintained. Matching pixel intensities may indicate that the intensity is due to X-ray scattered off of the object and is not blocked by the anti-scatter grid in either the first detector or the second detector. Because the pixel intensities match from the two differently oriented PCCT detector units, the signal may not be noise from internal scattering. Thus, the intensity may be maintained and used to produce an image. If it is determined that the pixel intensities do not match the pixel intensity is decreased. Because the pixel intensities from the two differently oriented PCCT detector units do not match (e.g., are not within the threshold difference), the signals may be noise due to internal scattering. Therefore, the pixel intensities are decreased to reduce noise in the resulting image after processing. In some examples, decreasing the pixel intensity may include decreasing the pixel intensity to zero.

In alternate examples, such as when count rates are higher, at 1010, method 1000 includes combining a projection image from intensities collected by the first orientation detector and from the intensities collected by the corresponding (e.g., neighboring or adjacent) second orientation detector. In one example, images may be combined by in the Fourier domain by taking X-direction frequencies from the projection images collected by the detector oriented to block scatter in the x-direction and Z-direction frequencies of projection images collected by the detector oriented to block scatter in the z-direction. As an alternate example, images may be combined using a neural network trained to extract the feature with the least amount of noise from each set of projection images.

Additionally or alternatively, combining intensities includes, at 1012 deconvoluting scatter noise from images collected by the first orientation detector and from the second orientation detector. Deconvoluting may include deconvoluting scatter noise from signal in the projection image. Deconvoluting may be performed by with a first deconvolution kernel configured to deconvolute images from the first orientation detector and by a second deconvolution kernel configured to deconvolute images from the second orientation detector. In some examples the deconvolution may occur before spectral and efficiency collection. In some examples, the corrected and deconvoluted images may additionally be combined as described above at step 1010. Method 1000 ends.

Figure 8:
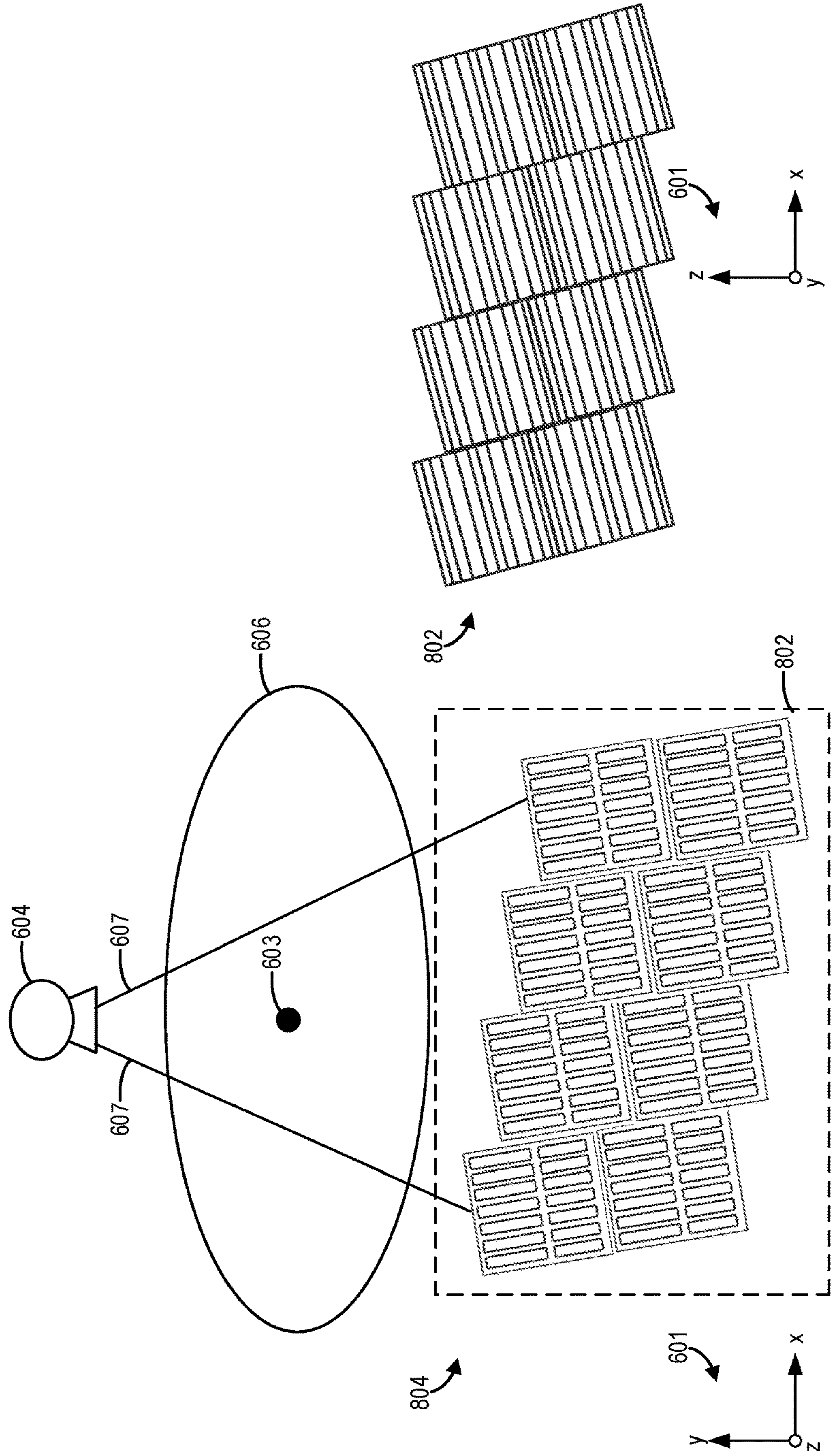
FIG. 8. shows a diagram of a third embodiment of an array of PCCT detector units.

Another alternate example of a detector array 802 is shown in FIG. 8, including a plurality of non-orthogonally oriented PCCT detector units 804. The non-orthogonally oriented PCCT detector units 804 may be the PCCT detector units 402 of FIGS. 4 and 5, arranged as shown in FIG. 8. For example, the orientation of the non-orthogonally oriented PCCT detector units 804 may be achieved by rotating the vertically oriented PCCT detector units 610 about the y-axis such that the sensors (e.g., sensors 302 of FIGS. 3-5) are at a non-orthogonal angle (e.g., less than 90 degrees) with the incident X-rays. Further non-orthogonal PCCT detector units 610 may be positioned with a stacking axis at an angle with respect to the axis of rotation. FIG. 8 shows the detector array 802 as viewed along the z-axis and relative X-ray source 604 and also shows detector array 802 as viewed along the y-axis. The detector units 804 may each be rotated to approximately the same angle such that the sensors thereof are parallel, with no other orientations of detector units in the detector array 802. Further, the detector units 804 may be side by side and in face sharing contact. In this way, noise may be reduced compared to conventionally oriented detectors. For example, in-plane scatter may be decreased at the expense of cross-plane scatter. Further, assembly and image reconstruction may be simplified by including detectors at one orientation instead of multiple orientations. In some examples the detector orientations shown in FIG. 8 may be combined with other detector orientations, such as those shown in FIGS. 6 and 7. The detector orientations of FIG. 8 may further be used in constructing a combined image as described above with respect to FIG. 10.

Figure 9:
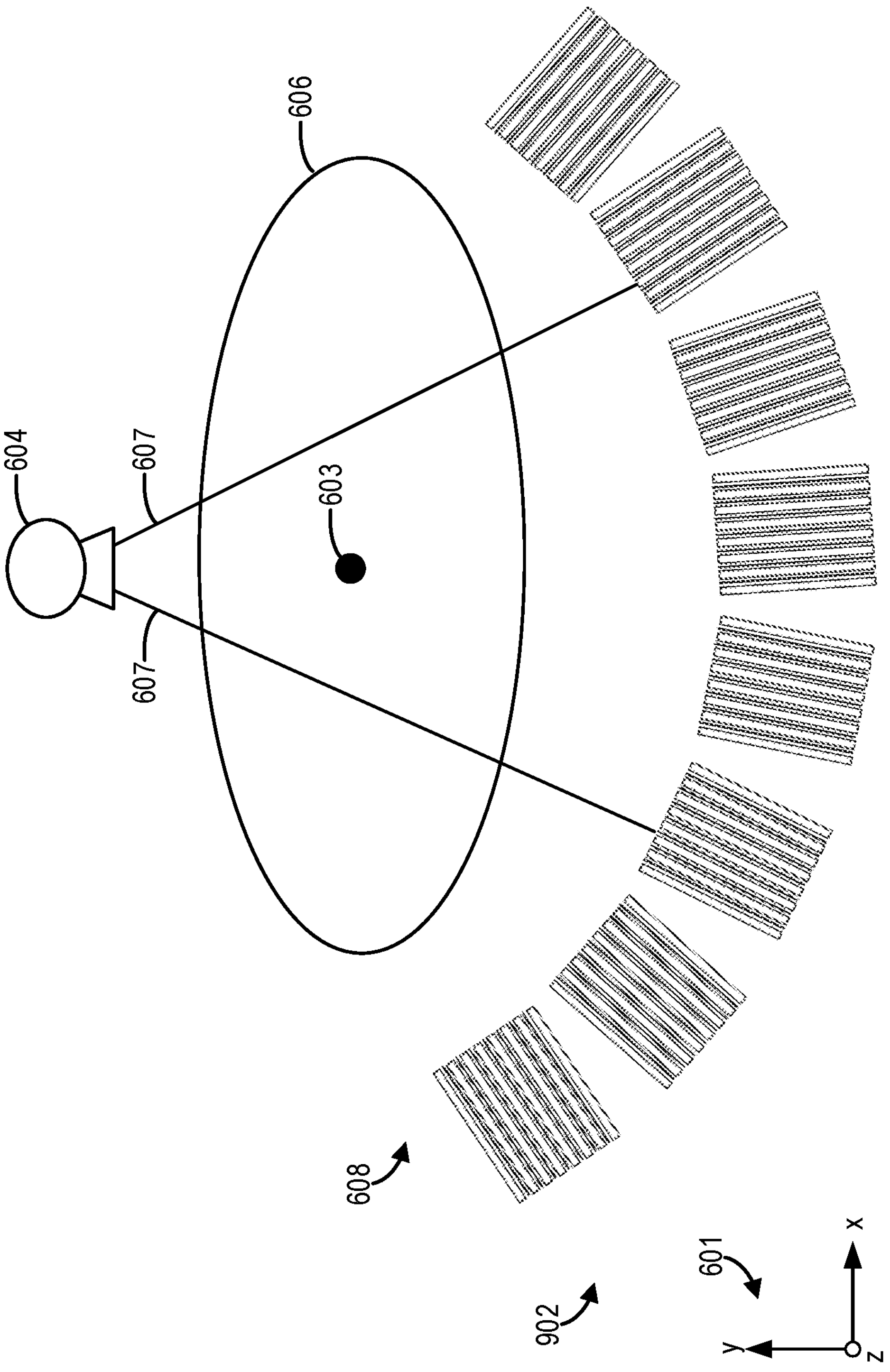
FIG. 9. shows a diagram of a fourth embodiment of an array of PCCT detector units.

Another alternate example of a detector array 902 is shown in FIG. 9, including a single row of horizontally oriented PCCT detector units 608, approximately equidistantly spaced away from the object 606. There may be no other orientations of detector units in the detector array 902. In this way, scattering may be reduced in the x-direction. In some examples, an X-Y slice of 3D volume may be of particular clinical relevance and reducing X-scatter may have more of a positive effect on clinical outcomes than reducing Z-scatter. In some examples, Z-scatter in detector array 902 may be reduced in a final image by applying a scatter correction algorithm before reconstructing images. Further, the scatter correction algorithm may be less computationally intensive than an algorithm configured to correct scatter in both the x and x directions. Additionally or alternatively, image volumes reconstructed after correcting for Z-scatter may exhibit higher image quality (e.g., increased resolution) not just in the trans-axial plane (e.g., X-Y slices), but also in the coronal (e.g., X-Z slices) and sagittal (e.g., Y-Z) planes.

Turning to FIG. 11, the sensor 302 is shown with a guard rings 1102 around a perimeter of the sensor 302. Guard rings 1102 may be omitted from depictions of sensor 302 in other figures for clarity purposes, but it is understood that any embodiment including sensor 302 may also include guard rings 1102. The guard ring 1102 may be positioned in face sharing contact with a face of sensor 302 in the x-y plane. The guard ring 1102 may have a height 1104, a width 1106, and a thickness 1108. The height 1104 and the width 1106 may change according to dimensions of the sensor 302, while the thickness 1108 may remain constant regardless of the dimensions of the sensor stack 401. The guard ring 1102 may protect the sensing units (e.g., diodes) from degradation, for example when incorporated into the detector unit 402 of FIG. 4 and used for imaging. For example, the guard rail may step down a potential across the sensor to prevent degradation of the diode. Additionally, the guard rail may protect the diodes from leakage current originating from side walls of sensor 302 flowing inwards towards the diodes.

Turning to FIG. 12, several sensor stacks 401 are shown with an incoming X-ray beam 301. Further, the sensor stacks may be vertically aligned and oriented with stacking axes parallel (e.g., in an x-direction). The sensors stacks 401 of each detector unit 402 may be wrapped in a metal foil 1204 made of a metal or metal alloy capable of absorbing scattered X-ray photons, for example a tungsten or tungsten alloy foil, such that surfaces in an x-y plane and surfaces in a y-z plane may be covered by the metal foil. Metal foil 1204 is shown partially transparent in FIG. 12 for clarity. Surfaces in the x-z plane of sensors 302 may be the surfaces struck by X-ray beam 301 and may not be covered by metal foil. Thus, the metal foil 1204 may be in face sharing contact with at least four surfaces of each detector unit. In this way, scattering may be reduced in the z-direction due to the fins 406 and in the x-direction between adjacent PCCT detector units (adjacent in the x-direction) 402 may be reduced due to the metal foil. To further reduce scattering in such a configuration, a dimension of the sensors 302 comprising the detector unit 402 may be decreased in the x-direction (e.g., a number of pixels) may be reduced and a number of detector units may be increased. In this way a number of interfaces between detector units may be increased and areas where scattering is decreased may also be increased. As shown in the graph 504, the plot 506 shows a peak in the x-direction without metal foil wrapped around the sensor stack 401, and a plot 1202 shows a peak in the x-direction with metal foil wrapped around the sensor stack 401. The peak in the plot 1202 is narrower due to scattering being limited in the x-direction by the metal foil. Thus, scattering of X-rays may be reduced relative to PCCT detector units which do not include the metal foil, resulting in a higher resolution image due to the metal foil.

An alternate example of a PCCT detector unit 1300 is shown in FIG. 13. In contrast to PCCT detector unit 402, PCCT detector unit 1300 may include fins (e.g., fins 406) positioned between alternating sensors 302 interfaces instead of between each sensor 302. Instead of fins, an adhesive layer 1302 may be present between two adjacent sensors at alternating sensor 302 interfaces. Adhesive layer 1302 may be configured to ensure fixed relative positioning between sensors 302 during installation and subsequent usage of the PCCT detector unit. Additionally, adhesive layer 1302 may reduce or narrow a solid angle of X-rays scattering in the x-y plane each sensor 302. Narrowing the solid angle may reduce a distance that an internally scattered X-ray may travel in the x-y plane of sensor 302.

Conventionally, adhesive may be applied in the x-y plane of each sensor in spaced apart lines along the x-axis of the sensor. However, having adhesive predominantly along a single axis of the sensor 302 may not efficiently reduce internal scatter in the x direction. For example, the cross section shown in FIG. 13 may include adhesive layer 1302 but a different cross section of PCCT detector unit 1300 (with adhesive lines in the x-direction) may have an empty gap in between sensors 302 and no adhesive.

Examples of a sensor including adhesive layers configured to reduce scattering of X-rays in the x-direction are shown in FIG. 14. A first sensor 1400 is shown including diagonal adhesive pattern 1402. Diagonal adhesive pattern 1402 may include a plurality of diagonal adhesive lines 1404. The plurality of diagonal adhesive lines 1404 may each be spaced apart and may be mutually parallel such that the diagonal adhesive lines 1404 do not intersect with each other. A second sensor 1430 may include a crosshatched adhesive pattern 1432. Crosshatched adhesive pattern 1432 may include a plurality of vertical adhesive lines 1434 spaced apart from each other and arranged parallel to the y-axis in addition to a plurality of horizontal adhesive lines 1436 spaced apart from each other and arranged parallel to the x-axis. Vertical adhesive lines 1434 and horizontal adhesive lines 1436 may intersect at multiple points on second sensor 1430, creating the crosshatched pattern. A third sensor 1460 may include an unbroken adhesive layer 1462. Unbroken adhesive layer 1462 may include adhesive extending continuously over an interior of the x-y plane of third sensor 1460. On each of first sensor 1400, second sensor 1430 and third sensor 1460, adhesive may not extend to an edge of the sensor and adhesive or the adhesive pattern may be positioned on the portion of the sensor including the sensor segments (e.g., sensor segments 305). In this way, along any cross section taken perpendicular to the stacking direction in the portion of the sensor including sensor segments (e.g., sensor segments 305), there may be at least a portion of the adhesive layer present. A pattern may be selected to balance reducing the solid angle in the x-direction with a time and cost associated with applying additional adhesive during manufacturing of the PCCT detector unit.

Additionally or alternatively the solid angle may be reduced in the x-direction by applying a layer of tungsten or other X-ray blocking material in to a backside (e.g., the surface in the x-y plane side not including the sensor segments 305) of the detector. In some examples the tungsten or tungsten alloy layer may be applied in a pattern similar to the adhesive patterns shown above with respect to FIG. 14. In some examples the tungsten layer may be added as a foil. In alternate examples the tungsten layer may be deposited by an additive thin film technique such as chemical vapor deposition.

Figure 15:
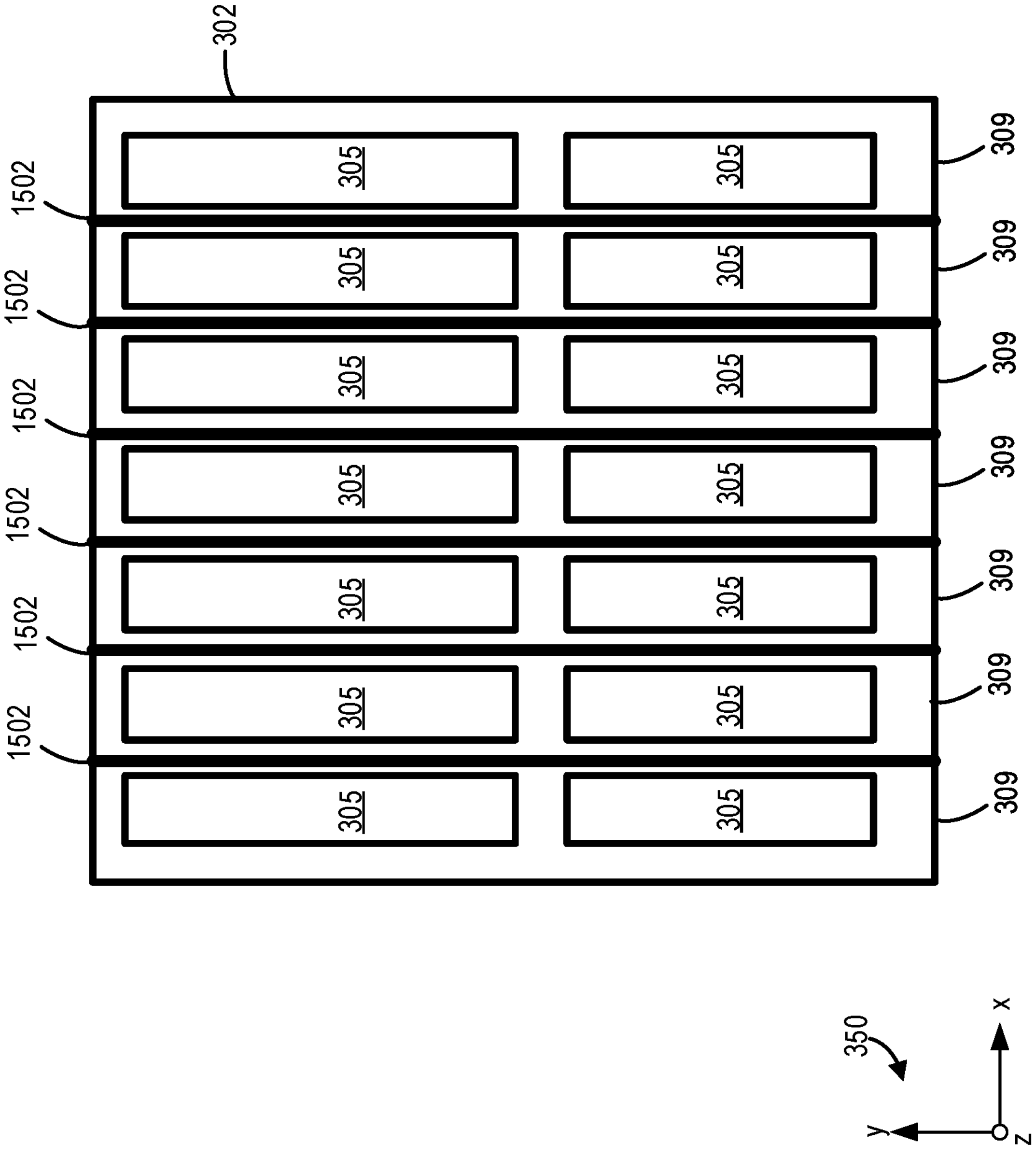
FIG. 15 shows a diagram of a sensor of a PCCT detector unit including trenches.
Figure 16:
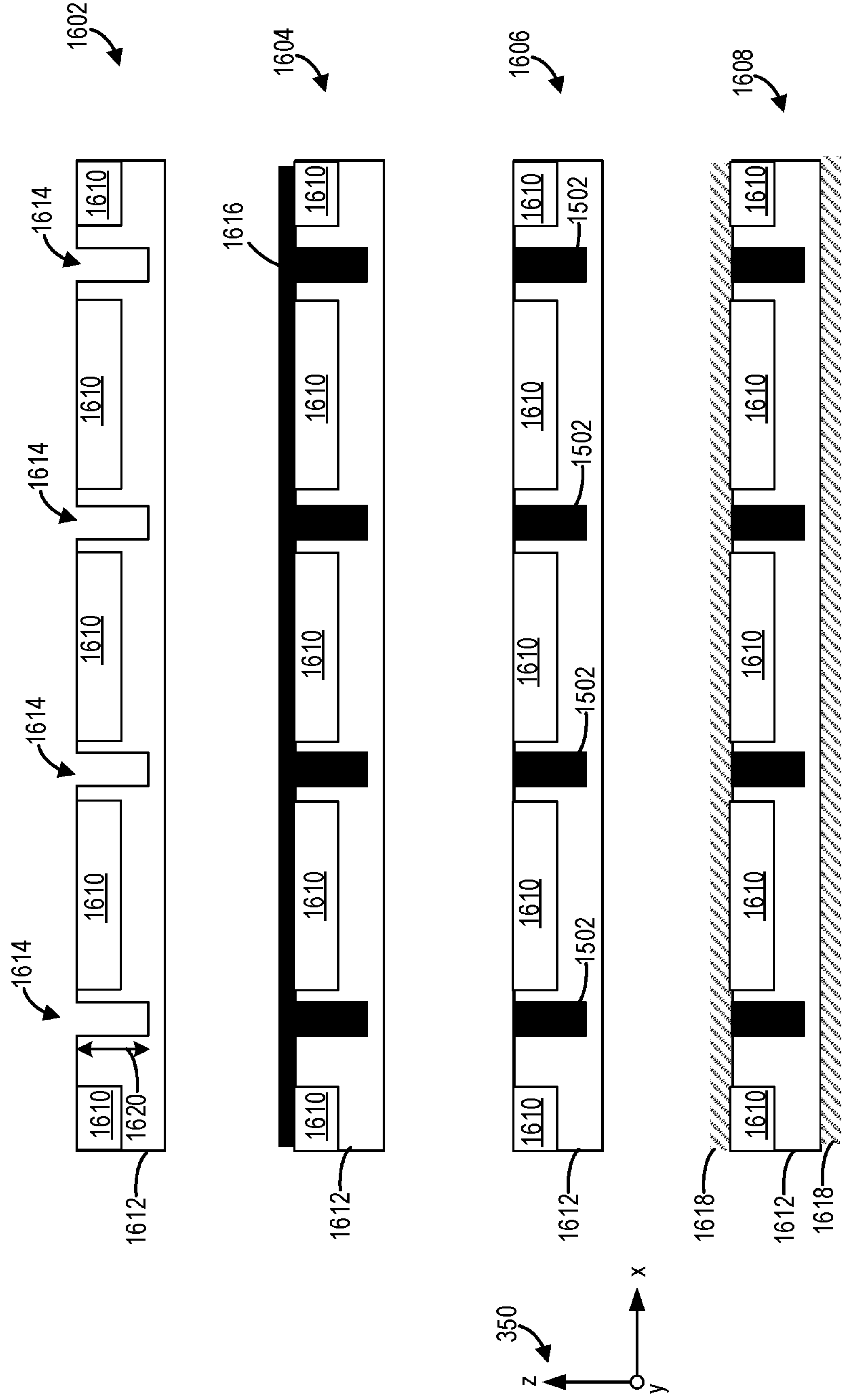
FIG. 16 shows a diagram of an example of process flow for forming trenches in the sensor.
Figure 17:
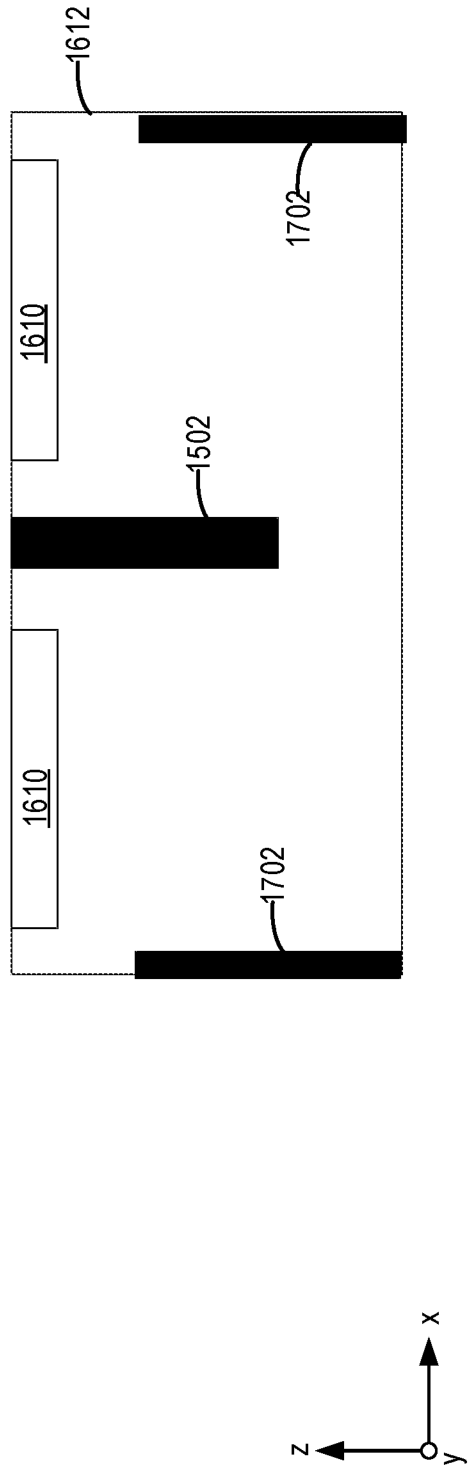
FIG. 17 shows an alternate example in trenches included on two sides of a wafer.

Additionally or alternatively, a sensor of a PCCT detector unit (e.g., PCCT detector unit 402) may incorporate X-ray blocking material into a sensor to block X-rays scattering in the x-direction. An example of incorporating X-ray blocking material into a sensor is shown in FIGS. 15-17. Turning now to FIG. 15, a sensor 302 is shown, viewed along the stacking axis (e.g., z-axis) including trenches 1502. Each trench 1502 may be at least partially filled with a high-atomic number, X-ray stopping material. As one example, the X-ray stopping material may be tungsten metal. In an alternate example, the post patient collimator may align with trenches 1502 and extend through sensor 302 to fill the trenches. As one example, 1502 trenches may be positioned between each pixel 309 of sensor 302. In alternate examples, trenches 1502 may be between alternating pixels or other arrangements. Further, trenches 1502 are shown in FIG. 15 extending an entire length in the y-direction of sensor 302, but in some examples, a length in the y-direction of trenches 1502 may be less than the length of the sensor. Placing trenches 1502 intermittently may allow for trace routing. In this way, trench 1502 may have an effect similar to fins 406, but blocking X-rays scattered in the x-direction instead of the z-direction. In some examples, trenches 1502 may be configured to align with fins 406. In this way, trenches 1502 may act as extensions of fins 406. Further a PCCT detector unit may be configured with a combination of trenches 1502 and fins 406 placed in a selected manor to work in a synergistic manner to minimize an amount of X-ray stopping material included in the PCCT detector unit while still maintaining a desired resolution of the X-ray image in both the x and y directions.

By incorporating the blocking material into the sensor other aspects of the PCCT detector unit and image processing methods may not demand adjustment. Additionally, due to trenches 1502 being behind (e.g., with respect to direction of X-ray travel) the post-patient collimator, geometric efficiency of the detector may not be affected. Because the X-ray stopping material may be an electrically conductive metal, trenches 1502 may also be used to carry signal.

An exemplary embodiment of a process flow for forming trenches 1502 in sensor 302 is shown in FIG. 16. FIG. 16 shows a cross-sectional view of a wafer 1612 used for forming a sensor of a PCCT detector unit, such as sensor 302. As an exemplary embodiment, wafer 1612 may be a silicon wafer. A first step, 1602, for forming trenches 1502 may be performed on wafer 1612 after diodes 1610 are formed on wafer 1612 but before addition of electrical wiring. Diodes 1610 may comprise the active photosensitive portions of the sensor. First step 1602 includes etching away wafer 1612 to form openings 1614. Openings 1614 may be a depth 1620 in the z-direction. In some examples depth 1620 may be less than a thickness of wafer 1612 in the z-direction. In alternate examples depth 1620 may be equal to the thickness of wafer 1612 in the z-direction and opening 1614 may be formed as via extending all the way through wafer 1612. Openings 1614 may become walls of trenches 1502. As one example openings 1614 may be etched by direct reactive ion-etching (DRIE), although other etching processes have also been considered.

An alternate example of wafer 1612 is shown in FIG. 17. In the alternate example, openings 1614 may be formed with an open side on the same side as diodes 1610 and with the open side facing the opposite side of wafer 1612 across the z-axis. When the openings are filled, both a trench 1502 and a reverse trench 1702 may be formed after openings 1614 are filled with X-ray stopping material. In one example a trench 1502 and a reverse trench 1702 may be formed between alternating diodes 1610. Forming trenches 1502 and reverse trenches 1702 may help reduce a strain on the wafer 16012. Further, reverse trench 1702 may help block X-ray scattering in the x-direction through an entire depth of the pixel.

In a second step 1604, an X-ray stopping material layer 1616 such as tungsten may be deposited on wafer 1612. During deposition the X-ray stopping material may fill each of openings 1614 and a surface of wafer 1612. In an alternate embodiment, one or more openings 1614 may be left unfilled by the X-ray stopping material layer 1616. Alternatively additional opening 1614 may be added after deposition of the X-ray material, thereby forming both empty and filled openings 1614. An opening 1614 without X-ray stopping material may prevent charge sharing between pixels of a sensor. X-ray stopping material layer 1616 may be in face sharing contact with diodes 1610 after second step 1604. Deposition of the X-ray stopping material layer 1616 may be performed by an additive thin layer process. As one example X-ray stopping material layer 1616 may be deposited by chemical vapor deposition. In alternate example, openings 1614 may be filled with a powdered X-ray stopping material, such as tungsten and the power may be sealed in place by a line of sealant, such as epoxy covering opening 1614 and not diodes 1610. In such an example, openings 1614 may be tapered to aid in powder filling. In further examples, powdered X-ray stopping material and sealant may be added in a plurality of layers within opening 1614 to avoid forming an equipotential.

Figure 18:
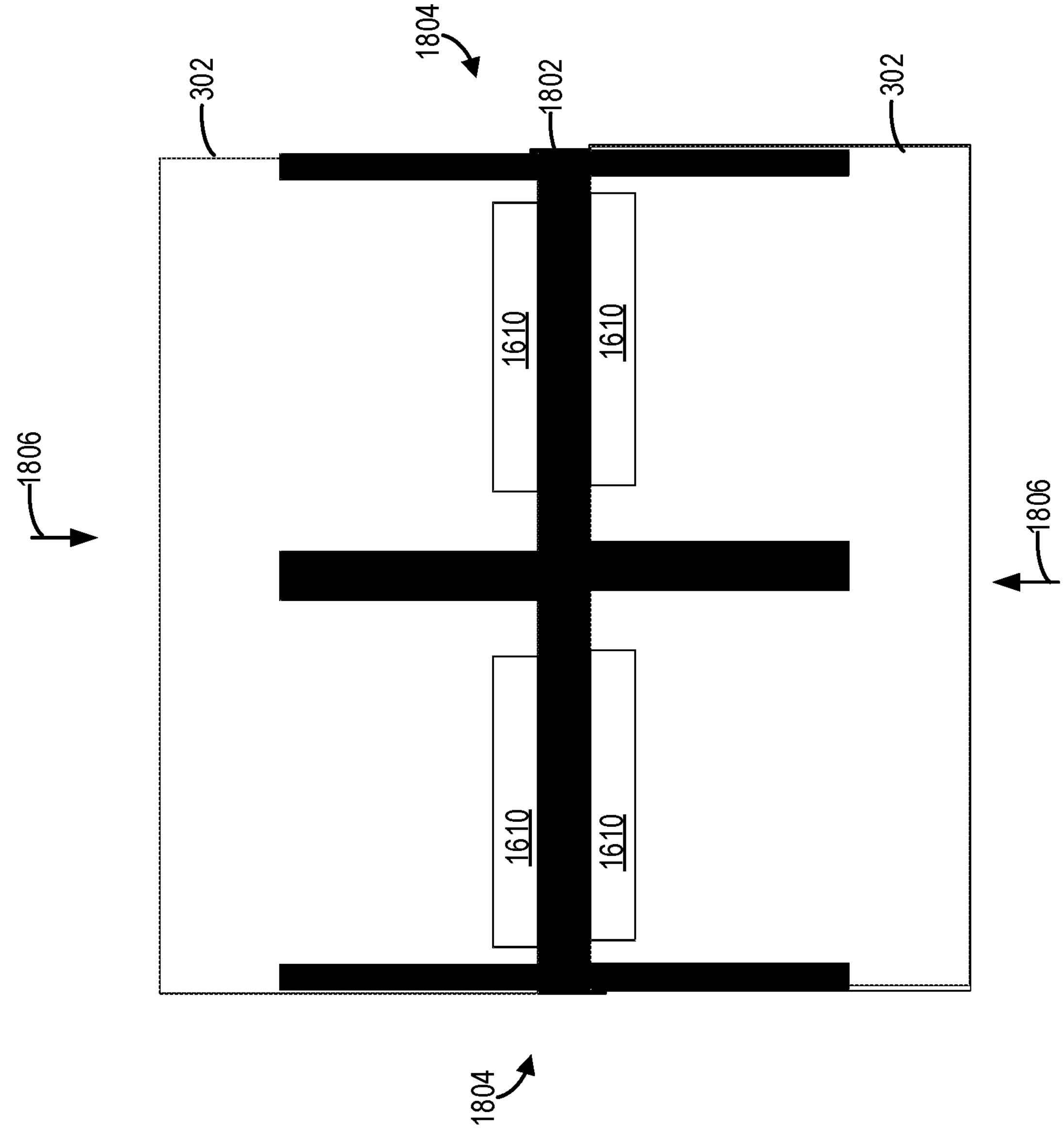
FIG. 18 shows a diagram of a sensor including a combination trench/blocking layer.

In an alternate example shown in FIG. 18, when sensors 302 are stacked in the PCCT detection unit a gap may be left between sensors 302 in the stacking direction. A flowable filler material may be injected from sides 1804 which may wick between sensors 302 and into openings 1614. The flowable filter material may formed of or include a substantial mass % of X-ray stopping material. In this way, a combination trench/blocking layer 1802 may be formed. In a further example, excess flowable filler material may be applied to a surface of sensors 302 and the flowable filter material may be forced into openings 1614 when pressure is applied to sensors 302 in the direction indicated by arrows 1806.

In a third step 1606, X-ray stopping material layer 1616 may be removed from a surface of wafer 1612 and left behind within openings 1614, thereby forming trenches 1502 within wafer 1612. As one example, X-ray stopping material layer 1616 may be removed from the surface by chemical mechanical polishing. In fourth step 1608, contact layers 1618 may be deposited on wafer 1612. After fourth step 1608, wafer 1612 may be ready for assembly into a sensor, such as sensor 302.

The technical effect of method 1000 is to decrease an amount of noise in X-ray image collected by an array of PCCT detector units. The method uses existing sensor hardware and takes advantage of relative positioning of the sensor hardware to decrease an amount of noise due to internal scatter. Further, systems described herein may place X-ray adsorbing elements, within, around, and between sensors of PCCT detector units to physically prevent crosstalk between pixels of a PCCT detector unit.

The disclosure also provides support for a computed tomography system, comprising: a gantry configured to rotate around an axis of rotation, and a detector array comprised of a plurality of photon-counting computed tomography (PCCT) detector units configured to be rotated with respect to the axis of rotation by the gantry, wherein a stacking axis of least one of the plurality of PCCT detector units is positioned at an angle with respect to the axis of rotation. In a first example of the system, the detector array comprises a number of horizontally oriented PCCT detector units positioned with a stacking axis perpendicular to the axis of rotation and a number of vertically oriented PCCT detector units positioned with a stacking axis parallel to the axis of rotation, configured such that X-rays scattered at an angle are detected by both the vertically oriented PCCT detector units and the horizontally oriented PCCT detector units, an wherein the number of vertically oriented detector units and the number of horizontally oriented detector units is equivalent. In a second example of the system, optionally including the first example, the detector array comprises a plurality of horizontally oriented PCCT detector units positioned with a stacking axis perpendicular to the axis of rotation and positioned in front of a plurality of vertically oriented PCCT detector units positioned with a stacking axis parallel to the axis of rotation such that X-rays scattered at an angle towards one of the plurality of horizontally oriented PCCT detector units also reaches one of the plurality of vertically oriented PCCT detector units. In a third example of the system, optionally including one or both of the first and second examples X-rays detected by the plurality of vertically oriented PCCT detector units are hardened with respect to the X-rays detected by the plurality of horizontally oriented PCCT detector units. In a fourth example of the system, optionally including one or more or each of the first through third examples, the detector array comprises an alternating pattern of horizontally oriented PCCT detector units positioned with a stacking axis perpendicular to the axis of rotation and vertically oriented PCCT detector units positioned with a stacking axis parallel to the axis of rotation, wherein X-rays scattered at an angle interact with one of a vertically oriented PCCT detector unit or a horizontally oriented PCCT detector unit. In a fifth example of the system, optionally including one or more or each of the first through fourth examples, the detector array comprises a plurality of non-orthogonally oriented PCCT detector units with stacking axes thereof parallel to one another and at an angle less than 90 degrees with respect to the axis of rotation. In a sixth example of the system, optionally including one or more or each of the first through fifth examples, the detector array comprises a plurality of horizontally oriented PCCT detector units positioned with a stacking axis perpendicular to the axis of rotation and does not include vertically oriented PCCT detector units positioned with a stacking axis positioned parallel to the axis of rotation. In a seventh example of the system, optionally including one or more or each of the first through sixth examples, the system further comprises: a controller configured to receive a first pixel intensity from a first orientation detector, receive a second pixel intensity from a corresponding second orientation detector, correct first pixel intensity and the second pixel intensity for spectral and efficiency differences, and combine intensities of the first orientation detector and the second orientation detector to from an image. In an eighth example of the system, optionally including one or more or each of the first through seventh examples, the first orientation detector is positioned in front of the corresponding second orientation detector such that X-rays scattered at an angle upon the detector array are detected by the first orientation detector and the corresponding second orientation detector. In a ninth example of the system, optionally including one or more or each of the first through eighth examples, the first orientation detector is adjacent to the corresponding second orientation detector such that the first orientation detector is at a different detection angle than the corresponding second orientation detector.

The disclosure also provides support for a photon-counting computed tomography (PCCT) detector unit, comprising: a sensor stack including a plurality of sensors stacked along a stacking axis, a metal foil in face sharing contact with four surfaces of the sensor stack, and wherein the four surfaces are perpendicular to faces of the plurality of sensors configured to receive X-rays. In a first example of the system, the metal foil is tungsten or tungsten alloy. In a second example of the system, optionally including the first example, the metal foil reduces X-ray scattering in a direction orthogonal to the stacking axis. In a third example of the system, optionally including one or both of the first and second examples, the metal foil reduces scatter between adjacent PCCT detector units relative to PCCT detector units without the metal foil. In a fourth example of the system, optionally including one or more or each of the first through third examples, the PCCT detector unit further comprises fins interposed between adjacent sensors.

The disclosure also provides support for a photon-counting computed tomography (PCCT) detector unit, comprising: a plurality of sensors stacked in a stacking direction, an adhesive layer positioned between two adjacent sensors of the plurality of sensors, wherein at least a portion of the adhesive layer is present in a cross section of the plurality of sensors taken perpendicular to the stacking direction. In a first example of the system, the system further comprises: a plurality of fins wherein each fin is interposed between two adjacent sensors. In a second example of the system, optionally including the first example, the adhesive layer comprises a plurality of diagonal adhesive lines. In a third example of the system, optionally including one or both of the first and second examples, the adhesive layer comprises a plurality of vertical adhesive lines and a plurality of horizontal adhesive lines, wherein the plurality of vertical adhesive lines and the plurality of horizontal adhesive lines intersect. In a fourth example of the system, optionally including one or more or each of the first through third examples, the adhesive layer comprises an unbroken adhesive layer.

In an alternate embodiment, the disclosure also provides support for a computed tomography system, comprising: a gantry configured to rotate around an axis of rotation, and a detector array comprised of a plurality of photon-counting computed tomography (PCCT) detector units configured to be rotated with respect to the axis of rotation by the gantry, wherein a stacking axis of least one of the plurality of PCCT detector units is positioned at an angle with respect to the axis of rotation. In a first example of the system, the system further comprises: a controller configured to receive a first pixel intensity from a first orientation detector, receive a second pixel intensity from a corresponding second orientation detector, correct first pixel intensity and the second pixel intensity for spectral and efficiency differences, and combine projection images formed by the first orientation detector and the second orientation detector.

In an alternate embodiment, the disclosure also provides support for a computed tomography system, comprising: a gantry configured to rotate around an axis of rotation, and a detector array comprised of a plurality of photon-counting computed tomography (PCCT) detector units configured to be rotated with respect to the axis of rotation by the gantry, wherein a stacking axis of least one of the plurality of PCCT detector units is positioned at an angle with respect to the axis of rotation. In a first example of the system, the system further comprises: a controller configured to receive a first pixel intensity from a first orientation detector, receive a second pixel intensity from a corresponding second orientation detector, correct first pixel intensity and the second pixel intensity for spectral and efficiency differences, and deconvolute scatter noise from the first orientation detector using a first filter kernel and from the second orientation detector using a second filter kernel.

As used herein, an element or step recited in the singular and preceded with the word “a” or “an” should be understood as not excluding plural of said elements or steps, unless such exclusion is explicitly stated. Furthermore, references to “one embodiment” of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

FIGS. 1-9 and 11-14 show example configurations with relative positioning of the various components. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space there-between and no other components may be referred to as such, in at least one example. As yet another example, elements shown above/below one another, at opposite sides to one another, or to the left/right of one another may be referred to as such, relative to one another. Further, as shown in the figures, a topmost element or point of element may be referred to as a "top" of the component and a bottommost element or point of the element may be referred to as a "bottom" of the component, in at least one example. As used herein, top/bottom, upper/lower, above/below, may be relative to a vertical axis of the figures and used to describe positioning of elements of the figures relative to one another. As such, elements shown above other elements are positioned vertically above the other elements, in one example. As yet another example, shapes of the elements depicted within the figures may be referred to as having those shapes (e.g., such as being circular, straight, planar, curved, rounded, chamfered, angled, or the like). Further, elements shown intersecting one another may be referred to as intersecting elements or intersecting one another, in at least one example. Further still, an element shown within another element or shown outside of another element may be referred as such, in one example.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A computed tomography system, comprising:

a gantry configured to rotate around an axis of rotation; and a detector array comprised of a plurality of photon-counting computed tomography (PCCT) detector units configured to be rotated with respect to the axis of rotation by the gantry, wherein a stacking axis of sensors of at least one of the plurality of PCCT detector units is positioned at an angle with respect to the axis of rotation, and wherein the plurality of PCCT detector units comprises a first number of horizontally oriented PCCT detector units with a first stacking axis of sensors perpendicular to the axis of rotation and a second number of vertically oriented PCCT detector units with a second stacking axis of sensors parallel to the axis of rotation, configured such that X-rays scattered at each detection angle are detected by both the vertically oriented PCCT detector units and the horizontally oriented PCCT detector units, and wherein the first number of vertically oriented detector units and the second number of horizontally oriented detector units is equivalent.

2. The computed tomography system of claim 1, wherein the detector array plurality of PCCT detector units comprises a plurality of horizontally oriented PCCT detector units positioned with a first stacking axis of sensors perpendicular to the axis of rotation and positioned in front of a plurality of vertically oriented PCCT detector units positioned with a second stacking axis of sensors parallel to the axis of rotation such that X-rays scattered at an angle towards one of the plurality of horizontally oriented PCCT detector units also reaches one of the plurality of vertically oriented PCCT detector units.

3. The computed tomography system of claim 2, X-rays detected by the plurality of vertically oriented PCCT detector units are hardened with respect to the X-rays detected by the plurality of horizontally oriented PCCT detector units.

4. The computed tomography system of claim 1, wherein the detector array plurality of PCCT detector units comprises a plurality of horizontally oriented PCCT detector units positioned with a first stacking axis of sensors perpendicular to the axis of rotation and vertically oriented PCCT detector units positioned with a second stacking axis of sensors parallel to the axis of rotation, wherein X-rays scattered at an angle interact with one of a vertically oriented PCCT detector unit or a horizontally oriented PCCT detector unit.

5. The computed tomography system of claim 1, wherein the detector array comprises a plurality of non-orthogonally oriented PCCT detector units with stacking axes of sensors thereof parallel to one another and at an angle less than 90 degrees with respect to the axis of rotation.

6. The computed tomography system of claim 1, wherein detector array plurality of PCCT detector units comprises a plurality of horizontally oriented PCCT detector units positioned with a first stacking axis of sensors perpendicular to the axis of rotation and does not include vertically oriented PCCT detector units positioned with a second stacking axis of sensors positioned parallel to the axis of rotation.

7. The computed tomography system of claim 1, further comprising a controller configured to:

receive a first pixel intensity from a first orientation detector of the plurality of PCCT detector units;

receive a second pixel intensity from a corresponding second orientation detector of the plurality of PCCT detector units;

correct first pixel intensity and the second pixel intensity for spectral and conversion efficiency differences; and combine intensities from the first orientation detector and the second orientation detector to form an image.

8. The computed tomography system of claim 7, wherein the first orientation detector is positioned in front of the corresponding second orientation detector such that X-rays scattered at an angle upon the detector array are detected by the first orientation detector and the corresponding second orientation detector.

9. The computed tomography system of claim 7, wherein the first orientation detector is adjacent to the corresponding second orientation detector such that the first orientation detector is at a different detection angle than the corresponding second orientation detector.

10. A computed tomography system, comprising:

a gantry configured to rotate around an axis of rotation; and a detector array comprised of a plurality of photon-counting computed tomography (PCCT) detector units configured to be rotated with respect to the axis of rotation by the gantry, wherein a stacking axis of sensors of least one of the plurality of PCCT detector units is positioned at an angle with respect to the axis of rotation, and wherein the plurality of PCCT detector units comprises a plurality of non-orthogonally oriented PCCT detector units with stacking axes of sensors thereof parallel to one another and at an angle less than 90 degrees with respect to the axis of rotation.

11. A computed tomography system, comprising:

a gantry configured to rotate around an axis of rotation; and a detector array comprised of a plurality of photon-counting computed tomography (PCCT) detector units configured to be rotated with respect to the axis of rotation by the gantry, wherein a stacking axis of sensors of least one of the plurality of PCCT detector units is positioned at an angle with respect to the axis of rotation, and wherein the plurality of PCCT detector units comprises an alternating pattern of horizontally oriented PCCT detector units with a first stacking axis of sensors perpendicular to the axis of rotation and vertically oriented PCCT detector units with a second stacking axis of sensors parallel to the axis of rotation, wherein X-rays scattered at an angle interact with one of a vertically oriented PCCT detector unit or a horizontally oriented PCCT detector unit and the horizontally oriented PCCT detector units and vertically oriented PCCT detector units are positioned approximately equidistantly from an object being imaged by the computed tomography system.

* * * * *